US008623357B2

(12) United States Patent
Waldmann et al.

(10) Patent No.: US 8,623,357 B2
(45) **Date of Patent: *Jan. 7, 2014**

(54) THERAPEUTIC ANTIBODIES

(75) Inventors: Hermann Waldmann, Oxford (GB); Mark Raymond Frewin, Oxford (GB); Lisa Kim Gilliland, Midlothian (GB); Luis Richardo Simoes da Silva Graca, Oxford (GB)

(73) Assignee: Isis Innovation, Ltd., Oxford (GB)

( * ) Notice: Subject to any disclaimer, the term of this patent is extended or adjusted under 35 U.S.C. 154(b) by 557 days.

This patent is subject to a terminal disclaimer.

(21) Appl. No.: 12/316,621

(22) Filed: Dec. 15, 2008

(65) Prior Publication Data

US 2010/0015166 A1 Jan. 21, 2010

Related U.S. Application Data

(63) Continuation of application No. 09/979,948, filed as application No. PCT/GB01/04518 on Oct. 9, 2001, now Pat. No. 7,465,790.

(60) Provisional application No. 60/242,143, filed on Oct. 23, 2000.

(30) Foreign Application Priority Data

Oct. 9, 2000 (GB) .................................. 0024673.6

(51) Int. Cl.
*A61K 39/395* (2006.01)
(52) U.S. Cl.
USPC .................................... 424/130.1; 424/277.1

(58) Field of Classification Search
None
See application file for complete search history.

(56) References Cited

U.S. PATENT DOCUMENTS 4,732,863 A * 3/1988 Tomasi et al. ................ 424/1.53

OTHER PUBLICATIONS

Gilliland et al (J of Immunology, 1999, 162:3662-3671.*
Tao et al, J of immunology, 143:2595-2601, 1995.*
James et al , JMB, 289:293-301, 1999.*

* cited by examiner

*Primary Examiner* — Lei Yao
(74) *Attorney, Agent, or Firm* — Elliot M. Olstein; Raymond J. Lillie

(57) ABSTRACT

A pharmaceutical comprising a therapeutic protein that hinds to a therapeutic target, the protein being modified with a compound that inhibits binding of the protein to the therapeutic target, the modified protein being effective for reducing an immune response against the protein and for producing a therapeutic effect by binding to the therapeutic target. The therapeutic protein may be an antibody that includes an antibody combining site that binds to the therapeutic target.

4 Claims, 17 Drawing Sheets

```
                                              MIM        Linker
  1  SLALQLLSTQ DLTMGWSCII LFLVATATGV HS QTSSPSAD GGGGSGGGGS

CDR1
 51  DIQMTQSPSS LSASVGDRVT ITCKASQNID KYL NWYQQKP GKAPKLLIY N

CDR2                                         CDR3
101  TNNLQT GVPS RFSGSGSGTD FTFTISSLQP EDIATYYC LQ HISRPRTEGQ

Light chain constant region
151  GTKVEIKTVA APSVFIFPPS DEQLKSGTAS VVCLLNNFYP REAKVQWKVD

201  NALQSGNSQE SVTEQDSKDS TYSLSSTLTL SKADYEKHKV YACEVTHQGL

251  SSPVTKSFNR GEC*KL
```

FIG. 7

```
                                                                    H
                                                                    i
      E                        B                                    n
      c                        a                                    d
      o                        m                                    I
      R                        H                                    I
      I                        I                                    I
      GAATTCGAGCTCGGTACCCGGGGATCCTCTAGAGTCGACCTGCAGGCATGC AAGCTTGGC
      ---------+---------+---------+---------+---------+---------+
      CTTAAGCTCGAGCCATGGGCCCCTAGGAGATCTCAGCTGGACGTCCGTACGTTCGAACCG b    N   S   S   S   V   P   G   D   P   L   E   S   T   C   R   H   A   S   L   A   -

Start   CP-1L Leader sequence
      TCTACAGTTACTGAGCACACAGGACCTCACC ATGGGATGGAGCTGTATCATCCTCTTCTT
      ---------+---------+---------+---------+---------+---------+
      AGATGTCAATGACTCGTGTGTCCTGGAGTGGTACCCTACCTCGACATAGTAGGAGAAGAA b    L   Q   L   L   S   T   Q   D   L   T   M   G   W   S   C   I   I   L   F   L   -

Mimotope              Gly4Serx2
      GGTAGCAACAGCTACAGGTGTCCACTC CCAAACCAGCAGCCCCTCAGCAGA CGGAGGTGG
      ---------+---------+---------+---------+---------+---------+
      CCATCGTTGTCGATGTCCACAGGTGAGGGTTTGGTCGTCGGGGAGTCGTCTGCCTCCACC b    V   A   T   A   T   G   V   H   S   Q   T   S   S   P   S   A   D   G   G Linker
      CGGATCCGGTGGAGGCGGAAG CGACATCCAGATGACCCAGAGCCCAAGCAGCCTGAGCGC
      ---------+---------+---------+---------+---------+---------+
      GCCTAGGCCACCTCCGCCTTCGCTGTAGGTCTACTGGGTCTCGGGTTCGTCGGACTCGCG b    G   S   G   G   G   S   D   I   Q   M   T   Q   S   P   S   S   L   S   A   -

CDR1
      CAGCGTGGGTGACAGAGTGACCATCAC CTGTAAAGCAAGTCAGAATATTGACAAATACTT
      ---------+---------+---------+---------+---------+---------+
      GTCGCACCCACTGTCTCACTGGTAGTGGACATTTCGTTCAGTCTTATAACTGTTTATGAA b    S   V   G   D   R   V   T   I   T   C   K   A   S   Q   N   I   D   K   Y   L   -

CDR2
      AAACTGGTACCAGCAGAAGCCAGGTAAGGCTCCAAAGCTGCTGATCTA CAATACAAACAA
      ---------+---------+---------+---------+---------+---------+
      TTTGACCATGGTCGTCTTCGGTCCATTCCGAGGTTTCGACGACTAGATGTTATGTTTGTT b    N   W   Y   Q   Q   K   P   G   K   A   P   K   L   L   I   Y   N   T   N   N   -

TTTGCAAAC GGGTGTGCCAAGCAGATTCAGCGGTAGCGGTAGCGGTACCGACTTCACCTT
      ---------+---------+---------+---------+---------+---------+
      AAACGTTTGCCCACACGGTTCGTCTAAGTCGCCATCGCCATCGCCATGGCTGAAGTGGAA b    L   Q   T   G   V   P   S   R   F   S   G   S   G   S   G   T   D   F   T   F   -
```

FIG. 8A

```
                                                             CDR3
     CACCATCAGCAGCCTCCAGCCAGAGGACATCGCCACCTACTACT GCTTGCAGCATATAAG
     ---------+---------+---------+---------+---------+---------+
     GTGGTAGTCGTCGGAGGTCGGTCTCCTGTAGCGGTGGATGATGACGAACGTCGTATATTC b   T  I  S  S  L  Q  P  E  D  I  A  T  Y  Y  C  L  Q  H  I  S  -

TAGGCCGCGCAC GTTCGGCCAAGGGACCAAGGTGGAAATCAAAACTGTGGCTGGACCATC
     ---------+---------+---------+---------+---------+---------+
     ATCCGGCGCGTGCAAGCCGGTTCCCTGGTTCCACCTTTAGTTTTGACACCGACCTGGTAG b   R  P  R  T  F  G  Q  G  T  K  V  E  I  K  T  V  A  A  P  S  -

Light chain constant region
     TGTCTTCATCTTCCCGCCATCTGATGAGCAGTTGAAATCTGGAACTGCCTCTGTTGTGTG
     ---------+---------+---------+---------+---------+---------+
     ACAGAAGTAGAAGGGCGGTAGACTACTCGTCAACTTTAGACCTTGACGGAGACAACACAC b   V  F  I  F  P  P  S  D  E  Q  L  K  S  G  T  A  S  V  V  C  -

CCTGCTGAATAACTTCTATCCCAGAGAGGCCAAAGTACAGTGGAAGGTGGATAACGCCCT
     ---------+---------+---------+---------+---------+---------+
     GGACGACTTATTGAAGATAGGGTCTCTCCGGTTTCATGTCACCTTCCACCTATTGCGGGA b   L  L  N  F  Y  P  R  E  A  K  V  Q  W  K  V  D  N  A  L  -

CCAATCGGGTAACTCCCAGGAGAGTGTCACAGAGCAGGACAGCAAGGACAGCACCTACAG
     ---------+---------+---------+---------+---------+---------+
     GGTTAGCCCATTGAGGGTCCTCTCACAGTGTCTCGTCCTGTCGTTCCTGTCGTGGATGTC b   Q  S  G  N  S  Q  E  S  V  T  E  Q  D  S  K  D  S  T  Y  S  -

CCTCAGCAGCACCCTGACGCTGAGCAAAGCAGACTACGAGAAACACAAAGTCTACGCCTG
     ---------+---------+---------+---------+---------+---------+
     GGAGTCGTCGTGGGACTGCGACTCGTTTCGTCTGATGCTCTTTGTGTTTCAGATGCGGAC b   L  S  S  T  L  T  L  S  K  A  D  Y  E  K  H  K  V  Y  A  C  -

CGAAGTCACCCATCAGGGCCTGAGCTCGCCCGTCACAAAGAGCTTCAACAGGGGAGAGTG
     ---------+---------+---------+---------+---------+---------+
     GCTTCAGTGGGTAGTCCCGGACTCGAGCGGGCAGTGTTTCTCGAAGTTGTCCCCTCTCAC b   E  V  T  H  Q  G  L  S  S  P  V  T  K  S  F  N  R  G  E  C  -

H
        i
        n
        d
        I
        I
        I
     TTA GAAGCTT
     ---------+
     AATCTTCGAA
  b   *  K  L   -
```

FIG. 8B

```
                                                        H
                                                        i
                                                        n
                                                        d
                                                        I
                                                        I
                                                        I                              Start
       AAGCTTGGCTCTACAGTTACTGAGCACACAGGACCTCACC ATGGGATGGAGCTGTATCAT
       -----+---------+---------+---------+---------+---------+--
       TTCGAACCGAGATGTCAATGACTCGTGTGTCCTGGAGTGGTACCCTACCTCGACATAGTA b     S   L   A   L   Q   L   L   S   T   Q   D   L   T   M   G   W   S   C   I   I  -

CP-1L Leader sequence                        Gly4Serx2 Linker
       CCTCTTCTTGGTAGCAACAGCTACAGGTGTCCACTCCC AAGGAGGTGGCGGATCCGGTGG
       ---------+---------+---------+---------+---------+---------+-
       GGAGAAGAACCATCGTTGTCGATGTCCACAGGTGAGGGTTCCTCCACCGCCTAGGCCACC b     L   F   L   V   A   T   A   T   G   V   H   S   Q   G   G   G   G   S   G   G  -

AGGCGGAAG CGACATCCAGATGACCCAGAGCCCAAGCAGCCTGAGCGCCAGCGTGGGTGA
       ---------+---------+---------+---------+---------+---------+------
       TCCGCCTTCGCTGTAGGTCTACTGGGTCTCGGGTTCGTCGGACTCGCGGTCGCACCCACT b     G   G   S   D   I   Q   M   T   Q   S   P   S   S   L   S   A   S   V   G   D  -

CDR1
       CAGAGTGACCATCAC CTGTAAAGCAAGTCAGAATATTGACAAATACTT AAACTGGTACCA
       ---------+---------+---------+---------+---------+---------+
       GTCTCACTGGTAGTGGACATTTCGTTCAGTCTTATAACTGTTTATGAATTTGACCATGGT b     R   V   T   I   T   C   K   A   S   Q   N   I   D   K   Y   L   N   W   Y   Q  -

CDR2
       GCAGAAGCCAGGTAAGGCTCCAAAGCTGCTGATCTA CAATACAAACAATTTGCAAAC GGG
       ---------+---------+---------+---------+---------+---------+
       CGTCTTCGGTCCATTCCGAGGTTTCGACGACTAGATGTTATGTTTGTTAAACGTTTGCCC b     Q   K   P   G   K   A   P   K   L   L   I   Y   N   T   N   N   L   Q   T   G  -

TGTGCCAAGCAGATTCAGCGGTAGCGGTAGCGGTACCGACTTCACCTTCACCATCAGCAG
       ---------+---------+---------+---------+---------+---------+
       ACACGGTTCGTCTAAGTCGCCATCGCCATCGCCATGGCTGAAGTGGAAGTGGTAGTCGTC b     V   P   S   R   F   S   G   S   G   S   G   T   D   F   T   F   T   I   S   S  -

CDR3
       CCTCCAGCCAGAGGACATCGCCACCTACTACT GCTTGCAGCATATAAGTAGGCCGCGCAC
       ---------+---------+---------+---------+---------+---------+
       GGAGGTCGGTCTCCTGTAGCGGTGGATGATGACGAACGTCGTATATTCATCCGGCGCGTG
```

FIG. 9A b  L  Q  P  E  D  I  A  T  Y  Y  C  L  Q  H  I  S  R  P  R  T -

```
GTTCGGCCAAGGGACCAAGGTGGAAATCAAACGAACTGTGGCTGCACCATCTGTCTTCAT
---------+---------+---------+---------+---------+---------+
CAAGCCGGTTCCCTGGTTCCACCTTTAGTTTGCTTGACACCGACGTGGTAGACAGAAGTA
``` b  F  G  Q  G  T  K  V  E  I  K  R  T  V  A  A  P  S  V  F  I -

Light chain constant region
```
CTTCCCGCCATCTGATGAGCAGTTGAAATCTGGAACTGCCTCTGTTGTGTGCCTGCTGAA
---------+---------+---------+---------+---------+---------+
GAAGGGCGGTAGACTACTCGTCAACTTTAGACCTTGACGGAGACAACACACGGACGACTT
``` b  F  P  P  S  D  E  Q  L  K  S  G  T  A  S  V  V  C  L  L  N -

```
TAACTTCTATCCCAGAGAGGCCAAAGTACAGTGGAAGGTGGATAACGCCCTCCAATCGGG
---------+---------+---------+---------+---------+---------+
ATTGAAGATAGGGTCTCTCCGGTTTCATGTCACCTTCCACCTATTGCGGGAGGTTAGCCC
``` b  N  F  Y  P  R  E  A  K  V  Q  W  K  V  D  N  A  L  Q  S  G -

```
TAACTCCCAGGAGAGTGTCACAGAGCAGGACAGCAAGGACAGCACCTACAGCCTCAGCAG
---------+---------+---------+---------+---------+---------+
ATTGAGGGTCCTCTCACAGTGTCTCGTCCTGTCGTTCCTGTCGTGGATGTCGGAGTCGTC
``` b  N  S  Q  E  S  V  T  E  Q  D  S  K  D  S  T  Y  S  L  S  S -

```
CACCCTGACGCTGAGCAAAGCAGACTACGAGAAACACAAAGTCTACGCCTGCGAAGTCAC
---------+---------+---------+---------+---------+---------+
GTGGGACTGCGACTCGTTTCGTCTGATGCTCTTTGTGTTTCAGATGCGGACGCTTCAGTG
``` b  T  L  T  L  S  K  A  D  Y  E  K  H  K  V  Y  A  C  E  V  T -

H
i
n
d
I
I
I

```
CCATCAGGGCCTGAGCTCGCCCGTCACAAAGAGCTTCAACAGGGGAGAGTGTTAGAAGCT
---------+---------+---------+---------+---------+---------+
GGTAGTCCCGGACTCGAGCGGGCAGTGTTTCTCGAAGTTGTCCCCTCTCACAATCTTCGA
``` b  H  Q  G  L  S  S  P  V  T  K  S  F  N  R  G  E  C  *  K  L -

FIG. 9B

```
                                                        Linker
  1    VSLALQLLST QDLTMGWSCI ILFLVATATG VHSQ GGGGSG GGGS DIQMTQ CDR1                                    CDR2
 51    SPSSLSASVG DRVT ITCKAS QNIDKYL NWY QQKPGKAPKL LIY NTNNLQT

CDR3
101    GVPSRFSGSG SGTDFTFTIS SLQPEDIAT Y YCLQHISRPR T FGQGTKVEI

Light chain constant region
151    KRTVAAPSVF IFPPSDEQLK SGTASVVCLL NNFYPREAKV QWKVDNALQS

201    GNSQESVTEQ DSKDSTYSLS STLTLSKADY EKHKVYACEV THQGLSSPVT

251    KSFNRGEC*K LCSRLEFVDE LPIVS
```

FIG. 10

```
                                H
                                i
                                n
                                d
                                I
                                I
                                I                                            Start
            GCATCACTAGT AAGCTT GGCTCTACAGTTACTGAGCACACAGGACCTCACCATGGGATGG
            +----------+----------+----------+----------+----------+---------
            CGTAGTGATCATTCGAACCGAGATGTCAATGACTCGTGTGTCCTGGAGTGGTACCCTACC c              A  S  L  V  S  L  A  L  Q  L  L  S  T  Q  D  L  T  M  G  W  -

CP-1L Leader Sequence                                      HLA P61
            AGCTGTATCATCCTCTTCTTGGTAGCAACAGCTACAGGTGTCCACTCCCAAAGCCTGCTG
            +----------+----------+----------+----------+----------+---------
            TCGACATAGTAGGAGAAGAACCATCGTTGTCGATGTCCACAGGTGAGGGTTTCGGACGAC c              S  C  I  I  L  F  L  V  A  T  A  T  G  V  H  S  Q  S  L  L  -

Gly4Serx2 Linker
            CCAGCAATCGTGGAGCTGGGAGGTGGCGGATCCGGTGGAGGCGGAAG CGACATCCAGATG
            +----------+----------+----------+----------+----------+---------
            GGTCGTTAGCACCTCGACCCTCCACCGCCTAGGCCACCTCCGCCTTCGCTGTAGGTCTAC c              P  A  I  V  E  L  G  G  G  S  G  G  G  S  D  I  Q  M  -

CDR1
            ACCCAGAGCCCAAGCAGCCTGAGCGCCAGCGTGGGTGACAGAGTGACCATCACCTGTAAA
            +----------+----------+----------+----------+----------+---------
            TGGGTCTCGGGTTCGTCGGACTCGCGGTCGCACCCACTGTCTCACTGGTAGTGGACATTT c              T  Q  S  P  S  S  L  S  A  S  V  G  D  R  V  T  I  T  C  K  -

GCAAGTCAGAATATTGACAAATACTT AAACTGGTACCAGCAGAAGCCAGGTAAGGCTCCA
            +----------+----------+----------+----------+----------+---------
            CGTTCAGTCTTATAACTGTTTATGAATTTGACCATGGTCGTCTTCGGTCCATTCCGAGGT

A  S  Q  N  I  D  K  Y  L  N  W  Y  Q  Q  K  P  G  K  A  P  -
c
                              CDR2
            AAGCTGCTGATCTA CAATACAAACAATTTGCAAAC GGGTGTGCCAAGCAGATTCAGCGGT
            +----------+----------+----------+----------+----------+---------
            TTCSACGACTAGATGTTATGTTTGTTAAACGTTTGCCCACACGGTTCGTCTAAGTCGCCA

K  L  L  I  Y  N  T  N  N  L  Q  T  G  V  P  S  R  F  S  G  -
c
            AGCGSTAGCGGTACCGACTTCACCTTCACCATCAGCAGCCTCCAGCCAGAGGACATCGCC
            +----------+----------+----------+----------+----------+---------
```

FIG. 11A

```
                TCGCCATCGCCATGGCTGAAGTGGAAGTGGTAGTCGTCGGAGGTCGGTCTCCTGTAGCGG c      S   G   S   G   T   D   F   T   F   T   I   S   S   L   Q   P   E   D   I   A   -

ACCTACTACT GCTTGCAGCATATAAGTAGGCCGCGCAC GTTCGGCCAAGGGACCAAGGTG
           +---------+----------+----------+----------+----------+----------
           TGGATGATGA CGAACGTCGTATATTCATCCGGCGCGTG CAAGCCGGTTCCCTGGTTCCAC
                                                             Light chain constant region
    c      T   Y   Y   C   L   Q   H   I   S   R   P   R   T   F   G   Q   G   T   K   V   -

GAAATCAAACGAACTGTGGCTGCACCATCTGTCTTCATCTTCCCGCCATCTGATGAGCAG
           +---------+----------+----------+----------+----------+----------
           CTTTAGTTTGCTTGACACCGACGTGGTAGACAGAAGTAGAAGGGCGGTAGACTACTCGTC c      E   I   K   R   T   V   A   A   P   S   V   F   I   F   P   P   S   D   E   Q   -

TTGAAATCTGGAACTGCCTCTGTTGTGTGCCTGCTGAATAACTTCTATCCCAGAGAGGCC
           +---------+----------+----------+----------+----------+----------
           AACTTTAGACCTTGACGGAGACAACACACGGACGACTTATTGAAGATAGGGTCTCTCCGG c      L   K   S   G   T   A   S   V   V   C   L   L   N   N   F   Y   P   R   E   A   -

AAAGTACAGTGGAAGGTGGATAACGCCCTCCAATCGGGTAACTCCCAGGAGAGTGTCACA
           +---------+----------+----------+----------+----------+----------
           TTTCATGTCACCTTCCACCTATTGCGGGAGGTTAGCCCATTGAGGGTCCTCTCACAGTGT c      K   V   Q   W   K   V   D   N   A   L   Q   S   G   N   S   Q   E   S   V   T   -

GAGCAGGACAGCAAGGACAGCACCTACAGCCTCAGCAGCACCCTGACGCTGAGCAAAGCA
           +---------+----------+----------+----------+----------+----------
           CTCGTCCTGTCGTTCCTGTCGTGGATGTCGGAGTCGTCGTGGGACTGCGACTCGTTTCGT c      E   Q   D   S   K   D   S   T   Y   S   L   S   S   T   L   T   L   S   K   A   -

GACTACGAGAAACACAAAGTCTACGCCTGCGAAGTCACCCATCAGGGCCTGAGCTCGCCC
           +---------+----------+----------+----------+----------+----------
           CTGATGCTCTTTGTGTTTCAGATGCGGACGCTTCAGTGGGTAGTCCCGGACTCGAGCGGG c      D   Y   E   K   H   K   V   Y   A   C   E   V   T   H   Q   G   L   S   S   P   -
                                                                          Hind 111
           GTCACAAAGAGCTTCAACAGGGGAGAGTGTTAG AAGCTT TG
           +---------+----------+----------+----------+
           CAGTGTTTCTCGAAGTTGTCCCCTCTCACAATCTTCGAAAC c      V   T   K   S   F   N   R   G   E   C   *   K   L   -
```

FIG. 11B

STQDLTMGWS CIILFLVATA

HLA-P61     Linker                                         CDR1
TGVHSQSLLP AIVEL GGGGS GGGGS DIQMT QSPSSLSASV GDRVT ITCKA

CDR2
SQNIDKYL NW YQQKPGKAPK LLIY NTNNLQ T GVPSRFSGS GSGTDFTFTI

CDR3
SSLQPEDIAT YYCLQHISRP RT FGQGTKVE IKRTVAAPSV FIFPPSDEQL

Light chain constant region
KSGTASVVCL LNNFYPREAK VQWKVDNALQ SGNSQESVTE QDSKDSTYSL

SSTLTLSKAD YEKHKVYACE VTHQGLSSPV TKSFNRGEC* KLCSRLEFVD

ELPIVSRI*R P

FIG. 12

SEQUENCE LISTING

<160> NUMBER OF SEQ ID NOS: 16

<210> SEQ ID NO 1
<211> LENGTH: 263
<212> TYPE: PRT
<213> ORGANISM: artificial sequence
<220> FEATURE:
<223> OTHER INFORMATION: MIM-IgG1 synthetic construct

<400> SEQUENCE: 1

```
Ser Leu Ala Leu Gln Leu Leu Ser Thr Gln Asp Leu Thr Met Gly
  1               5                  10                  15

Trp Ser Cys Ile Ile Leu Phe Leu Val Ala Thr Ala Thr Gly Val
                 20                  25                  30

His Ser Gln Thr Ser Ser Pro Ser Ala Asp Gly Gly Gly Gly Ser
                 35                  40                  45
```

```
Gly Gly Gly Gly Ser Asp Ile Gln Met Thr Gln Ser Pro Ser Ser
             50                  55                  60

Leu Ser Ala Ser Val Gly Asp Arg Val Thr Ile Thr Cys Lys Ala
             65                  70                  75

Ser Gln Asn Ile Asp Lys Tyr Leu Asn Trp Tyr Gln Gln Lys Pro
             80                  85                  90

Gly Lys Ala Pro Lys Leu Leu Ile Tyr Asn Thr Asn Asn Leu Gln
             95                 100                 105

Thr Gly Val Pro Ser Arg Phe Ser Gly Ser Gly Ser Gly Thr Asp
            110                 115                 120

Phe Thr Phe Thr Ile Ser Ser Leu Gln Pro Glu Asp Ile Ala Thr
            125                 130                 135

Tyr Tyr Cys Leu Gln His Ile Ser Arg Pro Arg Thr Phe Gly Gln
            140                 145                 150

Gly Thr Lys Val Glu Ile Lys Thr Val Ala Ala Pro Ser Val Phe
            155                 160                 165

Ile Phe Pro Pro Ser Asp Glu Gln Leu Lys Ser Gly Thr Ala Ser
            170                 175                 180

Val Val Cys Leu Leu Asn Asn Phe Tyr Pro Arg Glu Ala Lys Val
            185                 190                 195

Gln Trp Lys Val Asp Asn Ala Leu Gln Ser Gly Asn Ser Gln Glu
            200                 205                 210

Ser Val Thr Glu Gln Asp Ser Lys Asp Ser Thr Tyr Ser Leu Ser
            215                 220                 225

Ser Thr Leu Thr Leu Ser Lys Ala Asp Tyr Glu Lys His Lys Val
            230                 235                 240

Tyr Ala Cys Glu Val Thr His Gln Gly Leu Ser Ser Pro Val Thr
            245                 250                 255

Lys Ser Phe Asn Arg Gly Glu Cys
            260

<210> SEQ ID NO 2
<211> LENGTH: 850
<212> TYPE: DNA
<213> ORGANISM: Artificial Sequence
<220> FEATURE:
<223> OTHER INFORMATION: DNA encoding MIM-IgG1 protein and cloning
      vector sequence

<400> SEQUENCE: 2
gaattcgagc tcggtacccg gggatcctct agagtcgacc tgcaggcatg caagcttggc      60
tctacagtta ctgagcacac aggacctcac catgggatgg agctgtatca tcctcttctt     120
ggtagcaaca gctacaggtg tccactccca accagcagcc cctcagcag  acggaggtgg     180 cggatccggt ggaggcggaa gcgacatcca gatgacccag agcccaagca gcctgagcgc     240
cagcgtgggt gacagagtga ccatcacctg taaagcaagt cagaatattg acaaatactt     300
aaactggtac cagcagaagc caggtaaggc tccaaagctg ctgatctaca atacaaacaa     360
tttgcaaacg ggtgtgccaa gcagattcag cggtagcgt agcggtaccg acttcacctt     420
caccatcagc agcctccagc cagaggacat cgccacctac tactgcttgc agcatataag     480
taggccgcgc acgttcggcc aagggaccaa ggtggaaatc aaaactgtgg ctgcaccatc     540
tgtcttcatc ttcccgccat ctgatgagca gttgaaatct ggaactgcct ctgttgtgtg     600
cctgctgaat aacttctatc ccagagaggc caaagtacag tggaaggtgg ataacgccct     660
ccaatcgggt aactcccagg agagtgtcac agagcaggac agcaaggaca gcacctacag     720
```

-continued

```
cctcagcagc accctgacgc tgagcaaagc agactacgag aaacacaaag tctacgcctg    780
cgaagtcacc catcagggcc tgagctcgcc cgtcacaaag agcttcaaca ggggagagtg    840
ttagaagctt                                                          850
```

<210> SEQ ID NO 3
<211> LENGTH: 780
<212> TYPE: DNA
<213> ORGANISM: Artificial sequence
<220> FEATURE:
<223> OTHER INFORMATION: DNA encoding linker peptide and cloning vector
      sequence

<400> SEQUENCE: 3

```
aagcttggct ctacagttac tgagcacaca ggacctcacc atgggatgga gctgtatcat     60
cctcttcttg gtagcaacag ctacaggtgt ccactcccaa ggaggtggcg atccggtgg    120 aggcggaagc gacatccaga tgacccagag cccaagcagc ctgagcgcca gcgtgggtga    180
cagagtgacc atcacctgta aagcaagtca gaatattgac aaatacttaa actggtacca    240
gcagaagcca ggtaaggctc aaagctgct gatctacaat acaaacaatt tgcaaacggg    300
tgtgccaagc agattcagcg gtagcggtag cggtaccgac ttcaccttca ccatcagcag    360
cctccagcca gaggacatcg ccacctacta ctgcttgcag catataagta ggccgcgcac    420
gttcggccaa gggaccaagg tggaaatcaa acgaactgtg gctgcaccat ctgtcttcat    480
cttcccgcca tctgatgagc agttgaaatc tggaactgcc tctgttgtgt gcctgctgaa    540
taacttctat cccagagagg ccaaagtaca gtggaaggtg gataacgccc tccaatcggg    600
taactcccag gagagtgtca cagagcagga cagcaaggac agcacctaca gcctcagcag    660
caccctgacg ctgagcaaag cagactacga gaaacacaaa gtctacgcct gcgaagtcac    720
ccatcagggc ctgagctcgc cgtcacaaaa gagcttcaac aggggagagt gttagaagct    780
```

<210> SEQ ID NO 4
<211> LENGTH: 258
<212> TYPE: PRT
<213> ORGANISM: Artificial Sequence
<220> FEATURE:
<223> OTHER INFORMATION: linker peptide

<400> SEQUENCE: 4

```
Val Ser Leu Ala Leu Gln Leu Leu Ser Thr Gln Asp Leu Thr Met
  1               5                  10                  15

Gly Trp Ser Cys Ile Ile Leu Phe Leu Val Ala Thr Ala Thr Gly
                 20                  25                  30

Val His Ser Gln Gly Gly Gly Ser Gly Gly Gly Ser Asp
                 35                  40                  45

Ile Gln Met Thr Gln Ser Pro Ser Ser Leu Ser Ala Ser Val Gly
                 50                  55                  60

Asp Arg Val Thr Ile Thr Cys Lys Ala Ser Gln Asn Ile Asp Lys
                 65                  70                  75

Tyr Leu Asn Trp Tyr Gln Gln Lys Pro Gly Lys Ala Pro Lys Leu
                 80                  85                  90

Leu Ile Tyr Asn Thr Asn Asn Leu Gln Thr Gly Val Pro Ser Arg
                 95                 100                 105

Phe Ser Gly Ser Gly Ser Gly Thr Asp Phe Thr Phe Thr Ile Ser
                110                 115                 120

Ser Leu Gln Pro Glu Asp Ile Ala Thr Tyr Tyr Cys Leu Gln His
                125                 130                 135
```

```
Ile Ser Arg Pro Arg Thr Phe Gly Gln Gly Thr Lys Val Glu Ile
            140                 145                 150

Lys Arg Thr Val Ala Ala Pro Ser Val Phe Ile Phe Pro Pro Ser
            155                 160                 165

Asp Glu Gln Leu Lys Ser Gly Thr Ala Ser Val Val Cys Leu Leu
            170                 175                 180

Asn Asn Phe Tyr Pro Arg Glu Ala Lys Val Gln Trp Lys Val Asp
            185                 190                 195

Asn Ala Leu Gln Ser Gly Asn Ser Gln Glu Ser Val Thr Glu Gln
            200                 205                 210

Asp Ser Lys Asp Ser Thr Tyr Ser Leu Ser Ser Thr Leu Thr Leu
            215                 220                 225

Ser Lys Ala Asp Tyr Glu Lys His Lys Val Tyr Ala Cys Glu Val
            230                 235                 240

Thr His Gln Gly Leu Ser Ser Pro Val Thr Lys Ser Phe Asn Arg
            245                 250                 255

Gly Glu Cys

<210> SEQ ID NO 5
<211> LENGTH: 821
<212> TYPE: DNA
<213> ORGANISM: Artificial Sequence
<220> FEATURE:
<223> OTHER INFORMATION: DNA encoding P61-IgG1 protein and cloning
      vector sequence

<400> SEQUENCE: 5
gcatcactag taagcttggc tctacagtta ctgagcacac aggacctcac catgggatgg      60
agctgtatca tcctcttctt ggtagcaaca gctacaggtg tccactccca aagcctgctg     120
ccagcaatcg tggagctggg aggtggcgga tccggtggag gcggaagcga catccagatg     180
acccagagcc caagcagcct gagcgccagc gtgggtgaca gagtgaccat cacctgtaaa     240
gcaagtcaga atattgacaa atacttaaac tggtaccagc agaagccagg taaggctcca     300
aagctgctga tctacaatac aaacaatttg caaacgggtg tgccaagcag attcagcggt     360
agcggtagcg gtaccgactt caccttcacc atcagcagcc tccagccaga ggacatcgcc     420
acctactact gcttgcagca tataagtagg ccgcgcacgt tcggccaagg gaccaaggtg     480
gaaatcaaac gaactgtggc tgcaccatct gtcttcatct tcccgccatc tgatgagcag     540
ttgaaatctg gaactgcctc tgttgtgtgc ctgctgaata acttctatcc cagagaggcc     600
aaagtacagt ggaaggtgga taacgccctc caatcgggta actcccagga gagtgtcaca     660
gagtaggaca gcaaggacag cacctacagc ctcagcagca ccctgacgct gagcaaagca     720
gactacgaga aacacaaagt ctacgcctgc gaagtcaccc atcagggcct gagctcgccc     780
gtcacaaaga gcttcaacag gggagagtgt tagaagcttt g                        821

<210> SEQ ID NO 6
<211> LENGTH: 259
<212> TYPE: PRT
<213> ORGANISM: Artificial sequence
<220> FEATURE:
<223> OTHER INFORMATION: P61-IgG1 - synthetic construct

<400> SEQUENCE: 6

Ser Thr Gln Asp Leu Thr Met Gly Trp Ser Cys Ile Ile Leu Phe
1               5                   10                  15

Leu Val Ala Thr Ala Thr Gly Val His Ser Gln Ser Leu Leu Pro
            20                  25                  30
```

```
Ala Ile Val Glu Leu Gly Gly Gly Ser Gly Gly Gly Ser
                35                  40                  45

Asp Ile Gln Met Thr Gln Ser Pro Ser Ser Leu Ser Ala Ser Val
                50                  55                  60

Gly Asp Arg Val Thr Ile Thr Cys Lys Ala Ser Gln Asn Ile Asp
                65                  70                  75

Lys Tyr Leu Asn Trp Tyr Gln Gln Lys Pro Gly Lys Ala Pro Lys
                80                  85                  90

Leu Leu Ile Tyr Asn Thr Asn Asn Leu Gln Thr Gly Val Pro Ser
                95                 100                 105

Arg Phe Ser Gly Ser Gly Ser Gly Thr Asp Phe Thr Phe Thr Ile
               110                 115                 120

Ser Ser Leu Gln Pro Glu Asp Ile Ala Thr Tyr Tyr Cys Leu Gln
               125                 130                 135

His Ile Ser Arg Pro Arg Thr Phe Gly Gln Gly Thr Lys Val Glu
               140                 145                 150

Ile Lys Arg Thr Val Ala Ala Pro Ser Val Phe Ile Phe Pro Pro
               155                 160                 165

Ser Asp Glu Gln Leu Lys Ser Gly Thr Ala Ser Val Val Cys Leu
               170                 175                 180

Leu Asn Asn Phe Tyr Pro Arg Glu Ala Lys Val Gln Trp Lys Val
               185                 190                 195

Asp Asn Ala Leu Gln Ser Gly Asn Ser Gln Glu Ser Val Thr Glu
               200                 205                 210

Gln Asp Ser Lys Asp Ser Thr Tyr Ser Leu Ser Ser Thr Leu Thr
               215                 220                 225

Leu Ser Lys Ala Asp Tyr Glu Lys His Lys Val Tyr Ala Cys Glu
               230                 235                 240

Val Thr His Gln Gly Leu Ser Ser Pro Val Thr Lys Ser Phe Asn
               245                 250                 255

Arg Gly Glu Cys

<210> SEQ ID NO 7
<211> LENGTH: 24
<212> TYPE: DNA
<213> ORGANISM: Artificial Sequence
<220> FEATURE:
<223> OTHER INFORMATION: PCR primer

<400> SEQUENCE: 7
cacagatgcg taaggagaaa atac                                       24

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
gcagtgagcg caacgcaat                                             19

<210> SEQ ID NO 9
<211> LENGTH: 60
<212> TYPE: DNA
<213> ORGANISM: Artificial sequence
<220> FEATURE:
<223> OTHER INFORMATION: PCR primer
```

<400> SEQUENCE: 9
gcttccgcct ccaccggatc cgccacctcc ttgggagtgg acacctgtag ctgttgctac    60

<210> SEQ ID NO 10
<211> LENGTH: 56
<212> TYPE: DNA
<213> ORGANISM: Artificial Sequence
<220> FEATURE:
<223> OTHER INFORMATION: PCR primer

<400> SEQUENCE: 10
ggaggtggcg gatccggtgg aggcggaagc gacatccaga tgacccagag cccaag    56

<210> SEQ ID NO 11
<211> LENGTH: 48
<212> TYPE: DNA
<213> ORGANISM: Artificial Sequence
<220> FEATURE:
<223> OTHER INFORMATION: PCR primer

<400> SEQUENCE: 11
gtctgctgat gggctgctgg tttgggagtg gacacctgta gctgttgc    48

<210> SEQ ID NO 12
<211> LENGTH: 48
<212> TYPE: DNA
<213> ORGANISM: Artificial sequence
<220> FEATURE:
<223> OTHER INFORMATION: PCR primer

<400> SEQUENCE: 12
caaaccagca gcccatcagc agacggaggt ggcggatccg gtggagga    48

<210> SEQ ID NO 13
<211> LENGTH: 50
<212> TYPE: DNA
<213> ORGANISM: Artificial sequence
<220> FEATURE:
<223> OTHER INFORMATION: PCR primer

<400> SEQUENCE: 13
ctccacgatt gctggcagca ggctttggga gtggacacct gtagctgttg    50

<210> SEQ ID NO 14
<211> LENGTH: 49
<212> TYPE: DNA
<213> ORGANISM: Artificial Sequence
<220> FEATURE:
<223> OTHER INFORMATION: PCR primer

<400> SEQUENCE: 14
agcctgctgc cagcaatcgt ggagctggga ggtggcggat ccggtggag    49

<210> SEQ ID NO 15
<211> LENGTH: 16
<212> TYPE: PRT
<213> ORGANISM: Artificial sequence
<220> FEATURE:
<223> OTHER INFORMATION: cloning vector sequence

<400> SEQUENCE: 15

Lys Leu Cys Ser Arg Leu Glu Phe Val Asp
 1               5                  10

Glu Leu Pro Ile Val Ser
            15

```
<210> SEQ ID NO 16
<211> LENGTH: 18
<212> TYPE: PRT
<213> ORGANISM: Artificial sequence
<220> FEATURE:
<223> OTHER INFORMATION: Cloning vector sequence

<400> SEQUENCE: 16

Lys Leu Cys Ser Arg Leu Glu Phe Val Asp
  1               5                  10

Glu Leu Pro Ile Val Ser Arg Ile
                15
```

THERAPEUTIC ANTIBODIES

This application is a continuation of application Ser. No. 09/979,948 filed Jul. 29, 2002, now U.S. Pat. No. 7,465,790, which is the national phase application of PCT Application No. PCT/GB01/04518, filed Oct. 9, 2001, which claims priority based on provisional patent application Ser. No. 60/242,143, filed Oct. 23, 2000, and United Kingdom Patent Application No. 0024673.6, filed Oct. 9, 2000, the contents of which are incorporated by reference in their entireties.

FIELD OF THE INVENTION

The present invention relates to therapeutic antibodies and to a method for reducing or eliminating their immunogenicity.

Tolerance to foreign antigen or tissue is a state whereby an otherwise normal, mature immune system is specifically unable to respond aggressively to that antigen/tissue which it therefore treats like a normal (non-diseased) body tissue/component. At the same time the immune system is competent to respond aggressively to foreign or diseased antigens/tissues to which it has not specifically tolerant either by the natural process of self-tolerance or by therapeutic tolerance induction procedures. A test for tolerance usually requires a demonstration that the tolerant individual fails to become immune to the specific antigen/tissue when one or preferably more attempts to immunize are made at a later time when the same individual can be shown to respond to an irrelevant antigen/tissue. As used herein, reference to induction of tolerance is also intended to encompass both complete and partial/incomplete tolerance induction. Complete tolerance induction involves the removal of the immune response to the antigen/tissue to which tolerance is to be induced where partial or incomplete tolerance induction involves a significant reduction in this immune response.

PRIOR ART

One of the major problems with the use of antibodies in therapy is the immune response mounted against them. As humans are naturally tolerant of their immunoglobulins, a number of strategies have been used to create human forms of therapeutic antibodies, strategies such as humanisation, phage display from human libraries, or the use of mice carrying human immunoglobulin gene repertoires. Although useful, these procedures cannot guarantee that patients do not still react against unique features of the therapeutic antibody, features such as the allotypic determinants in the constant regions, and idiotypic determinants encoded by the complementary-determining regions (CDRs).

Chiller and Weigle (1970) PNAS 65:551 showed in rodents that tolerance to foreign immunoglobulins can be induced by deaggregated monomers of those immunoglobulins whilst aggregates of such immunoglobulins were potentially immunogenic. Benjamin and Waldmann et al (1986) J. Exp. Med. 163:1539 showed that cell-binding antibodies could also be immunogenic compared to non-cell binding antibodies. Isaacs and Waldman (1994) Therapeutic Immunology 1:363-312 showed that the humoral response against therapeutic antibodies is CD4+ T-cell-dependent. To ensure that therapeutic antibodies are not immunogenic it would be desirable to induce tolerance in the CD4 T-cell population to all potentially immunogenic determinants of those therapeutic antibodies that host-cells might recognise.

Gilliland et al (1999) The Journal of Immunology 162: 3663-3671, described an alternative route to prevent immune response against therapeutic antibodies by pre-tolerising the host with a monomeric preparation of non-cell-binding antibody mutants. Specifically, this study showed that mutants of the anti-CD52 antibody CAMPATH-1H which are non-cell-binding lose immunogenicity and can consequently induce tolerance to wild-type binding antibodies. CAMPATH-1 is the generic name given to the CD52 glycoprotein antigen and to the family of antibodies that recognize this. CAMPATH is a registered trade mark. The unique ability of CAMPATH-1H antibodies to kill lymphocytes by both complement-mediated lysis and cell-mediated lysis has led to the extensive use of these antibodies for the serotherapy of lymphoma, marrow and organ transplantation and in the treatment of autoimmune diseases. The observation that some patients mount antiglobulin responses to the therapeutic antibody led to research aimed at abolishing immunogenicity. Gilliland et al. showed in murine models that the antiglobulin response to a cell-binding form of the CAMPATH-1H antibody could be abolished by first tolerizing with a non-cell binding mutant. However, to use this method therapeutically would require the application of two products, the non-binding tolerogen and the actual therapeutic antibody. This is a costly process and has the disadvantage that as the mutant and therapeutic antibodies differ in a few amino-acid residues and in some cases tolerance may not extend to the difference, so that an antiglobulin response could still arise to the wild-type (unmutated) antibody. There is therefore a need to ensure tolerance to the whole therapeutic antibody.

It has thus been a long-term goal in immunology to find a means to abolish the potential to mount an immune response to certain therapeutic proteins which may have amino-acid sequences different to the host. This would have major implications in a broad range of therapeutic areas ranging from cancer, to autoimmune disease to transplantation.

STATEMENT OF THE INVENTION

In accordance with one aspect of the present, there is provided a modified therapeutic antibody wherein the modified therapeutic antibody as compared to the unmodified antibody has a reduced binding to its target antigen. The reduced binding is such that over time the binding of the antibody to the target is increased.

According to one aspect, the present invention is directed to a therapeutic tolerising antibody which comprises a therapeutic antibody having a specific therapeutic effect wherein the antibody has been subject to a temporary obstruction of its antibody-combining site which reduces the binding of the antibody for its natural target and wherein following administration to a host the antibody is capable of regenerating sufficient of a functionally-competent form of the therapeutic antibody to achieve the said therapeutic effect, whereby the reduction of the binding of the antibody for its natural target renders the modified antibody tolerogenic to itself and to its functionally-competent form. In this respect, tolerogenic means that an immunogenic immune response (an antibody response) against the antibody is inhibited, reduced in severity and/or essentially eliminated.

Using this antibody the immunogenicity of cell-binding antibodies may be reduced or circumvented so that antibody therapy can be used to its full potential. Only one product is used which is one able to tolerise itself and produce the desired therapeutic effect. This eliminates the need for two products as used previously. The temporary blockade of the antibody combining site (ACS) of the antibody must be for a sufficient time to induce tolerance within the host immune system, i.e., inhibit the immunogenic immune response against the antibody, but once this has been achieved the antibody should revert to or regenerate a form which can interact with the therapeutic target by increasing the amount of antibody bound thereto. Thus, immunologically foreign antibodies may be given to produce the desired therapeutic effect with a reduction of and/or essentially eliminating a host immunogenic immune response to them. Thus, the generation of antibodies against the therapeutic antibody is reduced and/or essentially eliminated.

Thus, in accordance with an aspect of the invention, there is provided a pharmaceutical in the form of a therapeutic antibody wherein the therapeutic antibody includes an antibody combining site (ACS) for a therapeutic target and the antibody is modified with a compound that inhibits the binding of the therapeutic antibody to the therapeutic target.

In one such embodiment there is provided a therapeutic antibody that is modified to include a compound that is reversibly bound to the antibody combining site of the antibody, with the target antigen competing with the compound for binding to the ACS upon administration of the antibody, whereby binding of the antibody to the target is inhibited. In this manner, the amount of the modified antibody that becomes bound to the target antigen in the initial period after administration is less than would have become bound if the antibody was administered in its non-modified form. As the compound is displaced from the ACS as a result of competitive binding, the amount of antibody that becomes bound to the target antigen increases. By inhibiting the binding of the antibody, with the amount of antibody that is bound to the target increasing over time, the modified antibody is capable of reducing and/or essentially eliminating an antibody response thereto and is also capable of accomplishing the desired therapeutic effect.

In one embodiment, the modified antibody has an avidity for the target that is less than the avidity for the target of the unmodified, antibody. The avidity is reduced in an amount that is effective for reducing and/or eliminating an antibody response against the therapeutic antibody while producing the desired therapeutic effect by binding to the therapeutic target.

The term "therapeutic" as used herein encompasses both treating an existing disease condition or disorder and preventing and/or reducing the severity of a disease, condition or disorder.

A therapeutic target is the antigen to which the antibody binds, which antigen may or may not be present on a tissue or cells. The compound that is combined with the therapeutic antibody for inhibiting binding to the target may inhibit such binding by binding to the ACS and/or by binding or blocking access to the ACS; e.g., by steric hindrance.

The compound may be combined with the antibody by linking the compound to the antibody and/or by binding of the compound to the ACS. In one embodiment, the compound is linked or tethered to the antibody and also binds to the ACS. In another embodiment, the compound is linked to the antibody without binding to the ACS and inhibits binding of the antibody to the target by inhibiting access to the ACS; e.g., by steric hindrance. In one non-limiting embodiment, the compound is linked to only one of the chains of the antibody.

The therapeutic antibody may be used as a therapeutic in humans and may be a non-human antibody e.g. one raised in a rodent.

Chimeric and humanised, e.g. CDR-grafted, antibodies may be used in accordance with the present invention. These antibodies are less immunogenic than the corresponding rodent antibodies and thus temporary ACS blockade of such antibodies in accordance with the present invention may further reduce immunogenicity and enhance tolerogenicity.

The compound functions to inhibit binding of the antibody to the target whereby immediately after administration there is a reduction of the amount of antibody that binds to the target as compared to the amount of antibody that would bind without the presence of the compound. The amount of antibody that becomes bound to the target increases over time whereby in effect there is a temporary blocking of the ACS that inhibits the amount of antibody that binds to the target.

The temporary blockade of the ACS (a blockade that initially reduces the amount of antibody that binds to the target, with such amount increasing with time) may be effected by the following, including;

(i) Temporary occupancy with molecules such as the defined antigen or a domain thereof, low affinity antigenic peptides or mimotopes by pre-incubation in-vitro, that might gradually dissociate in-vivo, such that the antibody would gradually accumulate on cell-bound or other "target" antigen if the association and dissociation constants were favourable by comparison with the "obstructive" element; or (ii) Temporary occupancy with molecules such as the defined antigen or a domain thereof, low affinity antigenic peptides or mimotopes which may be attached by flexible linkers. Once administered in-vivo the antibody would gradually accumulate on cell-bound or other "target" antigen if the association and dissociation constants were favourable by comparison with the "obstructive" element; or (iii) Chemical drugs which may bind non-covalently in the ACS and be able to dissociate in-vivo; or (iv) Other changes that might temporarily obstruct the ACS.

Such a modification would interfere with antibody accumulation on the target antigen for a limited period, which would be enough to ensure that the administered therapeutic antibody has a tolerizing effect (which is at least a partial tolerizing effect) while allowing for the antibody to revert to or regenerate sufficient of its functionally-competent form to achieve the desired therapeutic effect, i.e., accumulate on the target antigen in an amount to produce such effect. Removal of the modification may also occur by the host's own physiological and biochemical processes such as pH changes, enzymatic cleavage within the host, natural competition with host antigens bound to cells. For example a peptide mimotope could be linked to the antibody H or L chain by a linker which carries an enzyme degradable motif, susceptible to cleavage by host enzymes, such as for example, leukocyte elastase, in-vivo.

According to one particularly advantageous embodiment of the invention the linker is cleaved by an enzyme which occurs only or preferentially at the desired site of action of the therapeutic antibody thereby providing selective delivery of the therapeutic antibody to the desired site of action. For example a linker cleaved by leukocyte elastase would be appropriate for an antibody whose intended site of action was the joints. Alternatively, soluble antigen or mimotope might dissociate more easily at low pH within the site of a tumour which may also provide selective delivery of the antibody to the desired site of action. Alternatively, a low affinity mimotope attached by an inert linker may naturally dissociate in-vivo, and reassociation may be prevented by the ACS interacting with the natural antigen on host cells Preferably, the native antigen, domains thereof, and peptide fragments or mimotopes are used to modify the ACS. The latter may be generated from peptide libraries either synthetically or biologically-derived. Non-covalently binding chemicals can be screened from natural or synthetic libraries or from other available products, for their ability to inhibit antibody binding to its antigen or a surrogate equivalent. The linkers which may be used are preferably flexible, but could be enzymatically cleavable and/or degradable by the body over a set time period.

The present invention is also directed to antibodies as described above further comprising an Fc region designed to reduce interaction with the complement system and with specialised cell receptors for the Fc region of immunoglobulins (FcR receptors). Part of the immunogenicity of cell-binding antibodies may come from their capacity to biologically activate the complement system and other cells which bind through FcR receptors. The removal of the biological effector functions in the Fc region of the antibody may reduce immunogenicity as compared to the unmodified antibody and thus enhance tolerogenicity. This will be useful for many antibodies where cell lysis is not essential, such as blocking or agonist antibodies. Thus, the addition of mutations in the ACS together with those in the Fc region may be the most effective at tolerisation towards Fc mutated antibodies designed to block or enhance cell-function.

According to a further aspect, the invention provides an antibody as defined above for use in therapy.

According to a still further aspect, the invention provides the use of an antibody as defined above in the manufacture of a medicament for use in the treatment of a mammal to achieve the said therapeutic effect. The treatment comprises the administration of the medicament in a dose sufficient to achieve the desired therapeutic effect. The treatment may comprise the repeated administration of the antibody.

According to a still further aspect, the invention provides a method of treatment of a human comprising the administration of an antibody as defined above in a dose sufficient to achieve the desired therapeutic effect and reduce and/or eliminate an antibody response to the therapeutic antibody. The therapeutic effect may be the alleviation or prevention of diseases which may include cancer, chronic inflammatory diseases such rheumatoid arthritis, autoimmune diseases such as diabetes, psoriasis, multiple sclerosis, systemic lupus and others, allergic diseases such as asthma, cardiovascular diseases such as myocardial infarction, stroke and infectious diseases. Indeed any disease where continuous or repeated doses of a therapeutic antibody are contemplated.

Temporary modification of the type described above may also be applicable to therapeutic proteins other than antibodies whose activity depends on a biologically active site which can be transiently blocked and where the activity of this site determines immunogenicity. Examples of such therapeutic proteins include hormones, enzymes, clotting factors, cytokines, chemokines, immunoglobulin-based fusion proteins.

When covalently linking the compound to the antibody, in one embodiment, the compound is preferably linked to only one of the two arms of the antibody.

The term "antibody" as used herein includes all forms of antibodies such as recombinant antibodies, humanized antibodies, chimeric antibodies, single chain antibodies, monoclonal antibodies etc. The invention is also applicable to antibody fragments that are capable of binding to a therapeutic target.

In one embodiment, a compound (which may be a peptide or other molecule that is capable of binding to the ACS of the antibody) is reversibly bound to the antibody binding or combining site of the antibody that is to be administered to a person. The compound occupies the binding site of the antibody for the antigen and thereby inhibits binding of the antibody to the antigen. Since the compound is reversibly bound to the antibody binding site, the antibody is capable of binding to the antigen against which the antibody is directed.

In one embodiment, the compound that is selected for binding to the antibody combining site of the antibody is one whereby the antibody avidity for the compound is less than the antibody avidity for the antigen. In this manner, when the antibody is initially administered, there will be reduced binding of the antibody to the antigen, as compared to the binding that would occur in the absence of the compound, with such binding increasing over time.

Applicant has found that reduction of an antibody response to a therapeutic antibody can be accomplished by administering an antibody that is capable of effectively binding to the antigen for producing the desired therapeutic effect, provided that during the period that immediately follows administration of the antibody, the amount of the antibody that binds to the antigen is reduced, with such amount being increased from the reduced amount over time.

Thus, unlike the prior art, in accordance with the invention, an antibody that is capable of performing its therapeutic function also reduces the immunogenic immune response against the antibody by initially reducing the amount of the therapeutic antibody binding to the antigen followed by an increase in the amount of the therapeutic antibody binding.

The compound that is used for binding to the antibody combining site in a manner that initially reduces the amount of antibody binding to the antigen may be a peptide. The peptide may be identical to or different from a corresponding peptide portion of the antigen to which the therapeutic antibody binds. The appropriate peptide for an antibody may be selected by testing a panel of peptides in an inhibition of binding assay with respect to the antibody and its antigen. These and other procedures should be known to those skilled in the art based on the teachings herein.

In one embodiment, the antibody combined with the compound has an avidity for the target antigen that is less than the avidity of the non-modified antibody for the target antigen. The relative avidity of the modified antibody and the unmodified antibody may be determined by an inhibition of binding assay using fifty percent binding inhibition as an end point. A modified antibody has a reduced avidity if there is an increase in the amount of modified antibody as compared to the amount of unmodified antibody required to produce a fifty percent inhibition of the binding of a labeled unmodified antibody to the target antigen.

The avidity of the modified antibody is reduced in an amount that is effective for reducing and/or essentially eliminating an antibody response against the antibody and the modified antibody has an avidity for the target that is effective for producing the desired therapeutic effect.

By way of non-limiting examples, the modified antibody as compared to the unmodified antibody has an avidity for the target antigen that is at least 4-fold less, and in many cases at least 50-fold less or at least 100-fold less than the avidity of the unmodified antibody for the target antigen.

In one non-limiting embodiment, the compound may inhibit binding of the modified antibody by providing a modified antibody with a reduced affinity for the target antigen as compared to the unmodified antibody. In one non-limiting embodiment, the modified antibody may have an affinity for the antigen to which it is to be bound that is at least two or at least five-fold less than the affinity of the unmodified antibody.

In many cases, the modified antibody may have an affinity that is at least ten-fold less or at least 20-fold less or at least 100 fold less than the unmodified antibody.

In one embodiment of the invention, the amount of the modified antibody that is administered is coordinated with the inhibition of binding of the modified antibody to the therapeutic target such that during the first 24 hours after administration the amount of modified antibody that is bound to the target antigen is less than the amount of modified antibody that is not bound to the target antigen, with such relative amounts being effective for reducing or eliminating the antibody response against the therapeutic antibody.

In many cases, without limiting the present invention, the modified antibody during the first twenty four hours or in some cases in the first 48 or 72 hours after administration thereof binds to the target antigen in an amount such that the ratio of the antibody that is not bound to the target to the antibody that is bound to the therapeutic target is at least 10:1 and in many cases is at least 50:1 or at least 100:1.

The modified antibody is employed in an amount that is effective for both producing the desired therapeutic effect and for inducing a reduced immune response against the antibody. In general, without limiting the present invention, the modified antibody is administered in an amount such that the quantity of the antibody administered during the 24-hour period that begins when the antibody is first administered is at least 50 mg and in general at least 100 mg and more generally at least 200 mg. The modified therapeutic antibody in many cases is used in an amount that is greater than the amount of the unmodified form required to achieve the desired therapeutic effect with such increased amount being used to provide an amount of modified therapeutic antibody that is not bound to the target antigen and is effective for reducing and/or essentially eliminating an immune response against the antibody in the recipient.

Thus, in accordance with an aspect of the present invention, there is a reduced immune response against a therapeutic antibody by modifying the antibody in a manner such that the antibody binds to its antigen, in vivo, in a reduced amount with such amount increasing over time. Applicant has found that a modified therapeutic antibody can perform its therapeutic function in vivo while also inducing a reduced immunogenic immune response against the antibody in vivo, provided that binding of the antibody to its antigen is inhibited or reduced immediately after administration thereof, with the binding increasing over time.

The therapeutic antibody may be employed in combination with a pharmaceutically acceptable carrier. The use of a suitable carrier is deemed to be within the skill of the art from the teachings herein.

The present invention is also directed to a therapeutic tolerising protein which comprises a protein having a specific therapeutic effect wherein the protein has a biologically active site which has been subject to a temporary obstruction which reduces the binding of the protein for its natural target and wherein following administration to a host the protein is capable of regenerating sufficient of a functionally-competent form of the therapeutic protein to achieve the said therapeutic effect, whereby the reduction of the binding of the protein for its natural target renders the modified protein tolerogenic to itself and to its functionally competent form.

The present invention is also directed to a method of modifying the pharmacokinetics of a therapeutic antibody or other protein such that its half-life is extended through longer-term presence as a free monomer. This is advantageous as a form of "slow release depot" in terms of cumulative doses and frequency of administration of the therapeutic protein needed to achieve desired therapeutic effects. In addition it also allows better tumour penetration and minimises some of the side-effects that follow antibody administration, effects resulting from immediate and massive accumulation of antibody on target cells.

The following Examples illustrate the invention. In the accompanying drawings:

FIG. 1 shows the results of binding studies which show that the form of CAMPATH-LH, with the mimotope bound by a flexible linker, is not able to bind to human T-cell line HUT78 which carries CD52 by comparison with forms of CAMPATH-LH carrying the linker alone (linker), an irrelevant peptide linked in the same way (p61-IgG1), the linker with mimotope attached (MIM-IgG1), as well as aglycosylated (removal of asparagine at position 297 of the H-chain) forms of the various antibodies (AG etc). It should be noted that AG.MIM-IgG1 form is also non-cell binding, and that the mere insertion of the linker itself reduces binding of CAMPATH-1H by about 4 fold.

FIG. 2 shows a Fluorescent Activated cell Sorter (FACS) dot-plot examining the binding of CAMPATH-1H antibody on the lymphocytes of CP-1-transgenic mice given various antibody constructs (0.5 mg) intraperitoneally (IP) 3 hours earlier. Peripheral blood and splenic lymphocytes were stained with an anti-human IgG1 to show up any accumulated antibody on their surface. In FIG. 2A we examined peripheral blood lymphocytes. Mice treated with the CAMPATH-1H and the AG-CAMPATH-1H form were very brightly stained, in fact saturated with antibody. Indeed some depletion of T-cells from the blood is seen at this stage with both constructs (4% and 32% of the lymphocytes being CD3+). The p61-IgG1 and AG-p61-IgG1 constructs also stain strongly, and achieve some depletion at this time (13.5% and 23% of the blood lymphocytes being CD3+). Mim-IgG1 stains the T-cells in the blood, albeit less effectively than the above constructs, and very little depletion is seen at this stage (65.7% of the lymphocytes are CD3+). Finally, the AG-MIM-IgG1 binds very weakly to blood lymphocytes and that weak binding is not associated with any T-cell depletion at this stage. In FIG. 2B comparable data are presented on splenic lymphocytes. Here we can see that both MIM-IgG1 and AG-MIM-IgG1 are extremely inefficient at binding and depletion unlike the other constructs that have achieved around 50% depletion by this stage.

FIG. 3 shows that even though the MIM-IgG1 and AG.MIM-IgG1 antibodies bind poorly to antigen in-vitro, they do bind to CD52+ cells (in CP-1 transgenic mice) in-vivo. 7 days after the administration of 500 μg of each antibody spleen and blood lymphocytes were analysed by flow cytometry. This figure shows that AG.MIM-IgG1 has bound to the CD3+ cells of the animal, and that the intensity of staining is higher than in FIG. 2. MIM-IgG1 has done the same but clearly some depletion has taken place as the percentage of CD3+ cells in the animals is less (1.7% in spleen vs 36.6% for AG.MIM-IgG1; and 16.1% in blood vs 78.9% for AG.MIM-IgG1).

FIG. 4 shows the effects, on peripheral blood lymphocyte counts, of treating mice transgenic for the CAMPATH-1 antigen (CP-1 mice) with different doses of CAMPATH-1H with (MIM-IgG1) or without the bound mimotope (CAMPATH-1H)). Peripheral blood lymphocytes (PBL) were analysed by flow cytometry. The left column shows the results of mice treated with 1 μg to 50 μg of antibody and the right column shows the results of the second experiment where animals were treated with 0.1 mg to 0.5 mg of antibody. The therapeutic antibody can kill host lymphocytes within 24 hours at doses down to 5 μg/ml whereas the antibody with mimotope bound is not able to do so with doses up to 250 μg/ml. In contrast at 21 days there are clear effects of depletion seen at the 250 μg and 500 μg doses of "with mimotope" while with the therapeutic antibody CAMPATH-1H lymphocytes are beginning to replenish the blood.

FIG. 5 shows the immunogenicity of the various antibody constructs in CP-1 transgenic mice. Sera were taken from CP-1 mice treated with different doses of test antibodies. Sera were collected 21 days (expt. A) or 28 days (expt. B) after administration and assessed for the presence of anti-CAMPATH-1H Abs by ELISA. Serum samples were diluted 1:20 in PBS 1% BSA and subsequently in two-fold dilutions. All doses of the therapeutic antibody CAMPATH-1H were immunogenic, while responses to all other modified forms were much lower (including p61-IgG1). Remarkably, 500 µg of the aglycosylated form with the mimotope (AG.MIM-IgG1) bound generated absolutely no response whatsoever. In Fig. B it can be seen that the failure of AG.MIM.IgG1 to immunise is not just the result of the mutation to remove the glycosylation of the FC region, as AG-CAMPATH-1H proved very immunogenic. The specificity of the effect for the mimotope was also clearly established as AG-p61-IgG1 was also quite immunogenic.

FIG. 6A examines the tolerogenicity of the various antibody constructs in CP-1 transgenic mice and shows the results of sera from CP1 mice treated with different doses of Ab at day 0 which were collected 30 days after challenge with 5 daily intraperitoneal injections of 50 µg of CAMPATH-LH and assessed for the presence of anti-CAMPATH-1H Abs by ELISA. Serum samples were diluted 1:20 in phosphate buffered saline (PBS) containing 1% BSA and subsequently titrated out in twofold dilutions. In the left hand figure mice were left 60 days before receiving the challenge CAMPATH-1H antibody, while in the right-hand figure they were left 21 days. The left figure (FIG. 5a) shows that animals pre-treated with any of 100, 250 or 500 µg doses of the mimotope were very impaired in their humoral response to CAMPATH-1H. This indicates some level of tolerisation. However, the right hand figure shows that mice were completely tolerised with the aglycosylated form of the MIM-binding antibody, but only partially impaired with the antibody binding the irrelevant peptide.

FIG. 6B examines the tolerogenic potential of the constructs are repeat boosting with the challenge antibody CAMPATH-1H. These are the results for the same animals seen in FIG. 5A, which had received a further challenge with 5 doses of 50 µg CAMPATH-1H antibody at the time of the previous sera collection. Sera from these animals were then collected 30 days after the rechallenge and analysed as described in FIG. 5. The conclusions are similar to those in FIG. 6A.

FIGS. 7 and 8 show the amino acid and nucleotide sequence respectively for the construct MIM-IgG1 used in the following examples (see also SEQ ID NO 1 and SEQ ID NO 2 which show the same sequence without annotations).

FIGS. 9 and 10 show the nucleotide and amino acid sequence respectively for the linker used in the following examples (see also SEQ ID NO 3 and SEQ ID NO 4 which show the same sequence without annotations).

FIGS. 11 and 12 show the nucleotide and amino acid sequence respectively for P61-IgG1 used in the following examples (see also SEQ ID NO 5 and SEQ ID NO 6 which show the same sequence without annotations).

EXAMPLES

Materials and Methods

The humanised anti-CD52 antibody CAMPATH-1H was used in the following experiments. Various constructs were made using the CAMPATH-1H antibody and the following methodology.

Generation of Non-Binding Variants of CAMPATH-1H:

The cloning of the V-regions of the humanised antibody CAMPATH-1H specific for the human CD52 antigen is performed as described in Gilliland et al (1999) The Journal of Immunology 162:33663-3671. The methodology is based on that of Orlandi et al., 1989, PNAS 86: 3833, using the polymerase chain reaction (PCR). The wild-type humanised CAMPATH-1 light chain was cloned into the vector pGEM 9 (Promega) and used as a PCR template for site-directed mutagenesis.

A flexible linker (Gly4Ser x 2) was added to the amino-terminal end of the light chain between the CAMPATH-1H leader sequence and CAMPATH-1H VL sequence using the oligonucleotide primers PUCSE2 and Link L-3'+Link-L-5' and PUCSE REV. The resulting fragments were PCR assembled using primers PUCSE2+PUCSE REV to give full length Linker-CP-1H light chain which could be cloned into expression vector as Hind111/Hind 111 fragment.

The Linker-CP-1H light chain construct was then used as a PCR template to generate the CD52 Mimotope QTSSPSAD and P61 SLLPAIVEL peptide constructs. Primers PUCSE2 and MIM-3'+CD52Mim-5' and PUCSE REV were used to give Mimotope-CP-1H light chain construct. Primers PUCSE2 and P61-3'+HuP61-5' and PUCSE REV were used to give P61-CP-1H light chain construct.

Linker-CP-1H, Mimotope-CP-1H, P61-CP-1H mutants were transferred to pBAN-2, a derivative of the pNH316 mammalian expression vector containing neomycin selection (Page et al. 1991 Biotechnology 9:64-68). and PEE 12 a mammalian expression vector containing the Glutamine Synthetase gene for selection Bebbington et al. 1992 Biotechnology 10:169-175.

Subconfluent dhfr$^-$ Chinese Hamster Ovary cells (Page et al. 1991 Biotechnology 9:64-68) or NSO mouse myeloma cells (ECACC cat no 8511503, Meth Enzymol 1981, 73B,3) were co-transfected with the light chain mutants and the CAMPATH-1H heavy chain construct with wild type human IgG1 constant region, aglycosyl human IgG1 constant region and Non FcR binding human IgG1 constant region.

CAMPATH-1H heavy chain constructs were expressed in pRDN-1 a variant of the pLD9 mammalian expression vector with a dhfr selectable marker (Page et al. 1991 Biotechnology 9:64-68) and PEE 12.

Transfection was carried out using LipofectAMINE PLUS reagent (Life Technologies) following the manufacturers recommendations.

Human IgG1 constant was derived from the wild type G1m (1,17) gene described by Takahashi et al., 1982 Cell 29, 671-679. Aglycosyl mutation at position 297 from asparagine to an alanine residue. Oligosaccharide at Asn-297 is a characteristic feature of all normal human IgG antibodies (Kabat et al, Sequence of proteins of immunological interest US Department of Health human services publication). Substitution of asparagine with alanine prevents the glycosylation of the antibody (Routledge and Waldman, Transplantation, 1995, 60). Non FcR binding mutation at position 235 from leucine to alanine and position 237 from glycine to alanine Xu et al., 1993 J Immunology 150: 152A. Substitution of leucine and glycine at positions 235 and 237 prevents complement fixation and activation.

Heavy and Light chain transfectants are selected for in hypoxanthine free IMDM containing 1 mg G418+5% (v/v) dialysed foetal calf serum. Resulting selected cells are screen for antibody production by ELISA and for antigen binding to human T cell clone HUT 78 Gootenberg J E et al. 1981 J. Exp. Med. 154: 1403-1418 and CD52 transgenic mice.

Cells producing antibody were cloned by limiting dilution, and then expanded into roller bottles cultures. The immunoglobulin from approximately 15 litres of tissue culture supernatant from each cell line is purified on protein A, dialysed against PBS and quantified.

List of Primers Used

| | | |
|---|---|---|
| PUCSE-2 | 5'-CAC AGA TGC GTA AGG AGA AAA TAC-3' | (SEQ ID NO 7) |
| PUCSE REV | 5'-GCA GTG AGC GCA ACG CAA T-3' | (SEQ ID NO 8) |
| LINK-L3' | 5'-GCT TCC GCC TCC ACC GGA TCC GCC ACC TCC TTG GGA GTG GAC ACC TGT AGC TGT TGC TAC-3' | (SEQ ID NO 9) |
| LINK-L5' | 5'-GGA GGT GGC GGA TCC GGT GGA GGC GGA AGC GAC ATC CAG ATG ACC CAG AGC CCA AG-3' | (SEQ ID NO 10) |
| MIM-3' | 5'-GTC TGC TGA TGG GCT GCT GGT TTG GGA GTG GAC ACC TGT AGC TGT TGC-3' | (SEQ ID NO 11) |
| CD52Mim-5' | 5'-CAA ACC AGC AGC CCA TCA GCA GAC GGA GGT GGC GGA TCC GGT GGA GGA-3' | (SEQ ID NO 12) |
| P61-3' | 5'-CTC CAC GAT TGC TGG CAG CAG GCT TTG GGA GTG GAC ACC TGT AGC TGT TG-3' | (SEQ ID NO 13) |
| HuP61- | 5'-AGC CTG CTG CCA GCA ATC GTG GAG CTG GGA GGT GGC GGA TCC GGT GGA G-3' | (SEQ ID NO 14) |

A blocking ligand was based on a published sequence of antibody peptide mimotope (Hale G 1995 Immunotechnology 1, 175-187) and was engineered into the wild-type CAMPATH-1H antibody as a cDNA sequence with a generic linker to attach the peptide product to the antibody light chain so as to enable the antibody to be secreted with its ligand bound in the antibody combining site. A similar antibody also had its Fc-region mutated so as to remove the glycosylation site at position 297.

Constructs/Cell Lines Produced

TF CHO/CP-1H IgG1/MIM and TF NSO/CP-1H IgG1/MIM (MIM IgG1)

Figure 1:
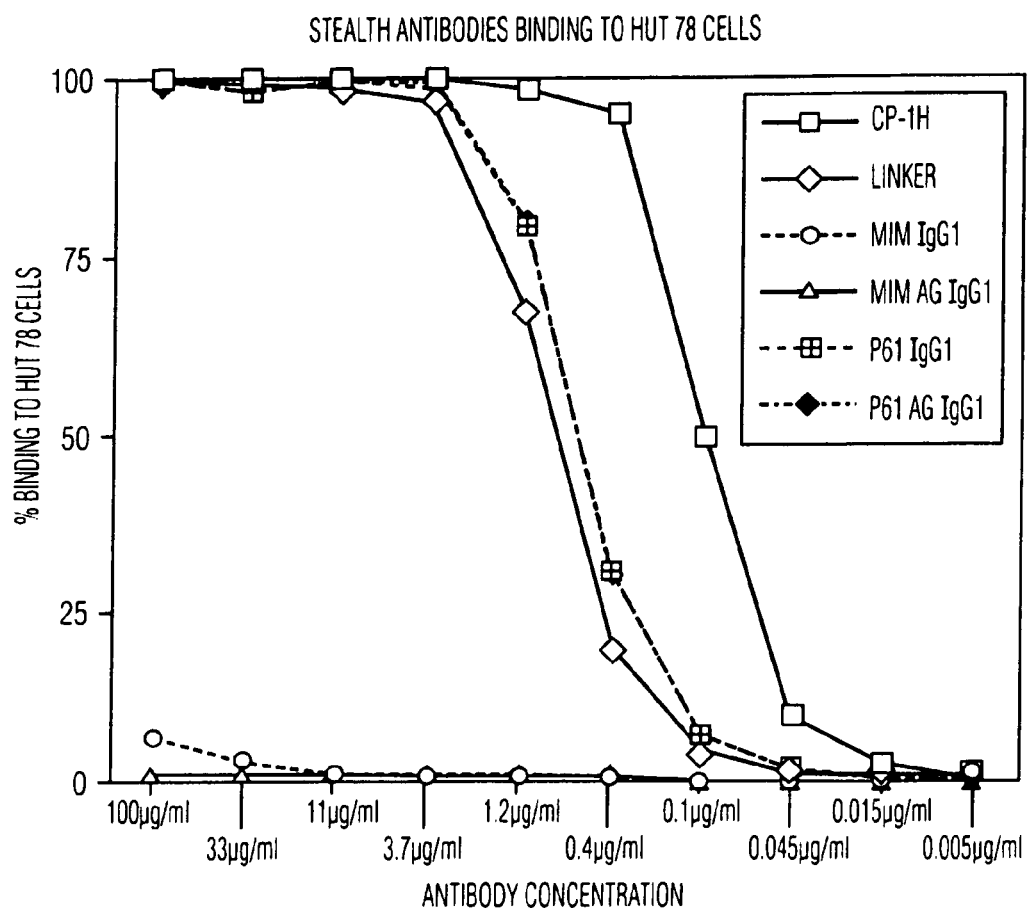
Figure 2A:
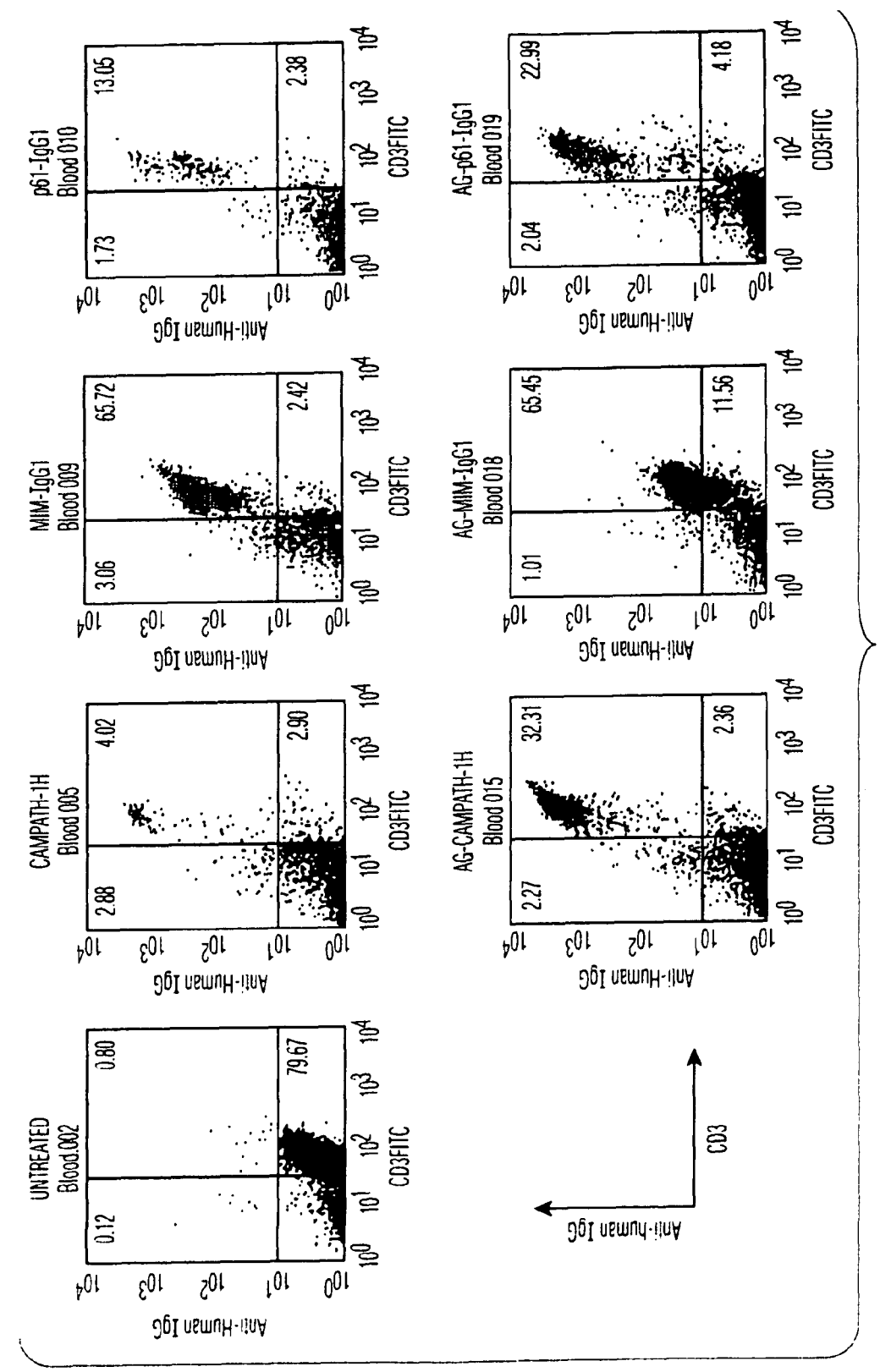
Figure 2B:
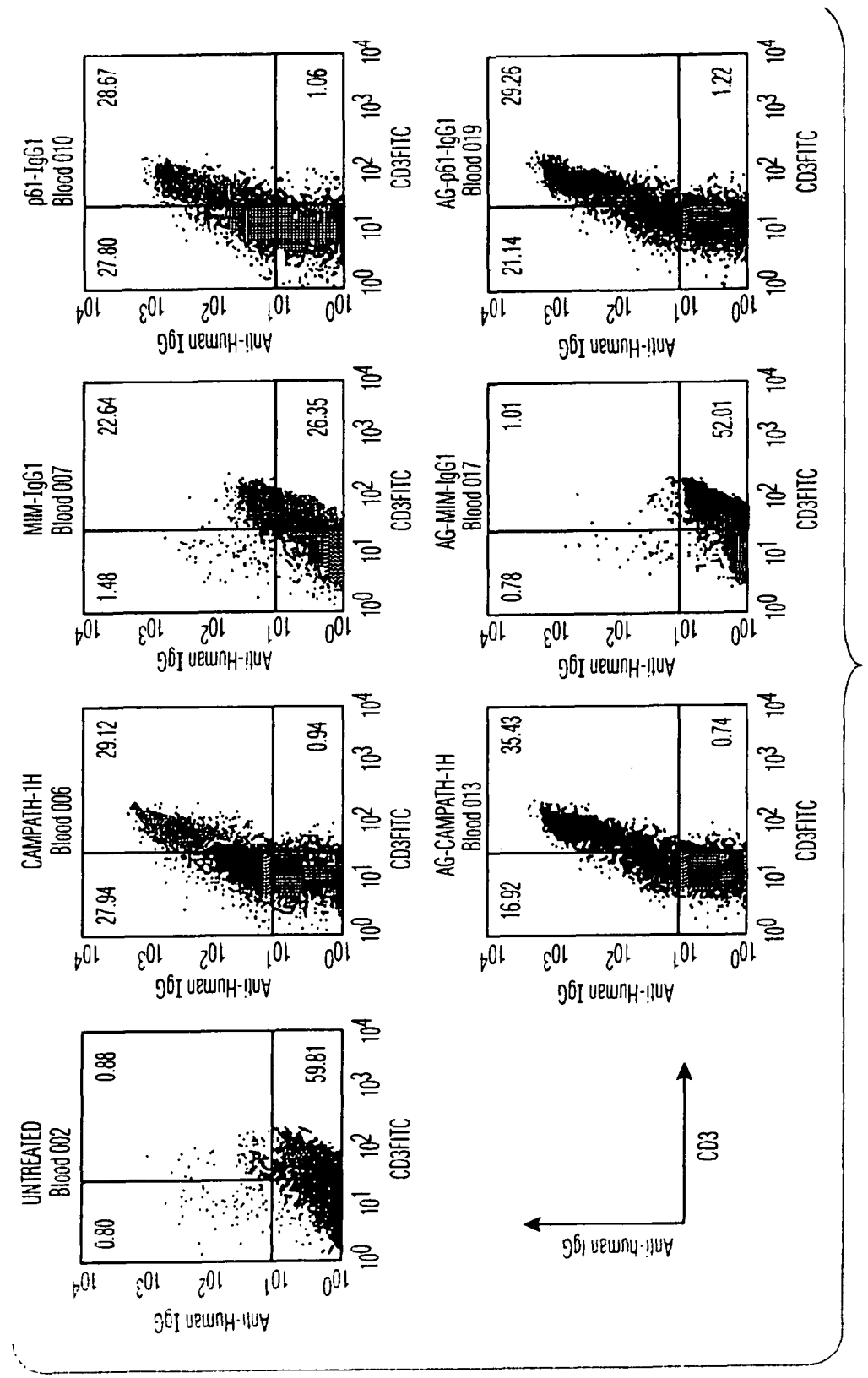

CD52 Mimotope QTSSPSAD (amino acid residues 33-40 of SEQ ID NO:1) tethered to CAMPATH-1H light chain V-region by flexible Glycine4 Serine x2 Linker+Campath-1H heavy chain with wild type human IgG1 constant region. Cloned into Celltech expression vector PEE12 for NSO produced antibody and Wellcome pRND-1 and pBAN-2 expression vectors for CHO produced antibody.

TF NSO/CP-1H AG IgG1/MIM (AG MIM IgG1)

CD52 Mimotope QTSSPSAD (amino acid residues 33-40 of SEQ ID NO:1) tethered to CAMPATH-1H light chain V-region by flexible Glycine4 Serine x2 Linker+CAMPATH-1 H heavy chain Aglycosyl human IgG1 constant region. Cloned into Celltech expression vector PEE12 for NSO produced antibody.

TF NSO/CP-1H FCR IgG1/MIM (FcRmutMIM IgG1)

CD 52 Mimotope QTSSPSAD (amino acid residues 33-40 of SEQ ID NO:1) tethered to CAMPATH-1 H light chain V-region by flexible Glysine4 Serine x2 Linker+CAMPATH-1H heavy chain FcR-MUTATED human IgG1 constant region. Cloned into Celltech expression vector PEE12 for NSO produced antibody.

TF CHO/CP-1H IgG1/Link (Linker)

Flexible Glycine4 Serine x2 Linker only on CAMPATH-1H light chain V-region+CAMPATH-1H heavy chain with wild type human IgG1 constant region.

Cloned into Wellcome expression vectors pRDN-1 and pBAN-2 for CHO produced antibody.

TF CHO/CP-1H IgG1/P61 (P61-IgG1)

HLA P61 binding peptide SLLPAIVEL (amino acid residues 27-35 of SEQ ID NO:6) (Hunt et al Science 1992 255 1261-1263) tethered to CAMPATH-1H light chain V-region by flexible Glycine4 Serine x2 Linker+CAMPATH-1H heavy chain with wild type human IgG1 constant region. Cloned into Wellcome expression vectors pRDN-1 and pBAN for CHO produced antibody.

TF NSO/CP-1H AG IgG1/P61 (AGP61 IgG1)

HLA P61 binding peptide SLLPAIVEL (amino acid residues 27-35 of SEQ ID NO:6) tethered to CAMPATH-1H light chain V-region by flexible Glycine4 Serine 2x Linker+CAMPATH-1H heavy chain with aglycosyl human IgG1 constant region. Cloned into Celltech expression vector PEE12 for NSO produced activity.

TF NSO/CP-1H FCR IgG1/P61 (FcRmut P61 IgG1)

HLA P61 binding peptide SLLPAIVEL (amino acid residues 27-35 of SEQ ID NO: 6) tethered to CAMPATH-1H light chain V-region by flexible Glycine4 Serine x2 Linker+CAMPATH-1H heavy chain with no FCR human IgG1 constant region. Cloned into Celltech expression vector PEE12 for NSO produced antibody.

TF CHO/CO-1H IgG1 (CAMPATH-1H)

Wild type CAMPATH-1H light chain V-region+CAMPATH-1H heavy chain with wild type human IgG1 constant region. Cloned into Wellcome expression vectors pRDN-1 and pBAN-2 for CHO produced antibody.

TF NSO/CP-1H AG IgG1 (AG-IgG1)

Wild type Campath01H light chain V-region+CAMPATH-1H heavy chain with aglycosyl human IgG1 constant region. Cloned into Celltech expression vector PEE12 for NSO produced antibody.

Results

A high dose of the purified, secreted products (CAMPATH-1H, MIM-IgG1, AG.MIM-IgG1) was injected into mice made transgenic for human CD52 (Gilliland et al). After one week the antibody could be found binding to cells in all 3 groups, whereas lymphocyte depletion could only be seen in the CAMPATH-1H and MIM-IgG1 groups.

Mice were then challenged with the wild-type antibody on multiple occasions and could mount only poor xenogenic humoral responses, unlike mice which had not received the tolerogen or mice that had, instead been treated with the wild-type CAMPATH-1H antibody from the outset. Mice tolerised with the aglycosylated form of MIM-IgG1 (AG-.MIM-IgG1) were completely unable to mount a xenogenic response even after 10 challenge doses of the therapeutic CAMPATH-1H antibody.

FIG. 1 shows the binding abilities of the various antibody constructs to CD52-bearing HUT cells. CAMPATH-1H binds with an efficiency approximately 2000 times superior to MIM-IgG1, 5 times than CAMPATH-1H-p61 (both P61-IgG1 and AG.P61-IgG1), and >10,000 times better than AG.MIM-IgG1.

FIG. 2 shows a Fluorescent Activated cell Sorter (FACS) dot-plot examining the binding of CAMPATH-1H antibody on the lymphocytes of CP-1-transgenic mice given various antibody constructs (0.5 mg) intraperitoneally (IP) 3 hours earlier. Peripheral blood and splenic lymphocytes were stained with an anti-human IgG1 to show up any accumulated antibody on their surface. In FIG. 2A we examined peripheral blood lymphocytes. Mice treated with the CAMPATH-1H and the AG-MIM-IgG1 form were very brightly stained, in fact saturated with antibody. Indeed some depletion of T-cells from the blood is seen at this stage with both constructs (4% and 32% of the lymphocytes being CD3+). The p61-IgG1 and AG-p61-IgG1 constructs also stain strongly, and achieve some depletion at this time (13.5% and 23% of the blood lymphocytes being CD3+). Mim-IgG1 stains the T-cells in the blood, albeit less effectively than the above constructs, and very little depletion is seen at this stage (65.7%) of the lymphocytes are CD3+). Finally, the AG-MIM-IgG1 binds very weakly to blood lymphocytes and that weak binding is not associated with any T-cell depletion at this stage. In FIG. 2B comparable data are presented on splenic lymphocytes. Here we can see that both MIM-IgG1 and AG-MIM-IgG1 are extremely inefficient at binding and depletion unlike the other constructs that have achieved around 50% depletion by this stage.

Figure 3:
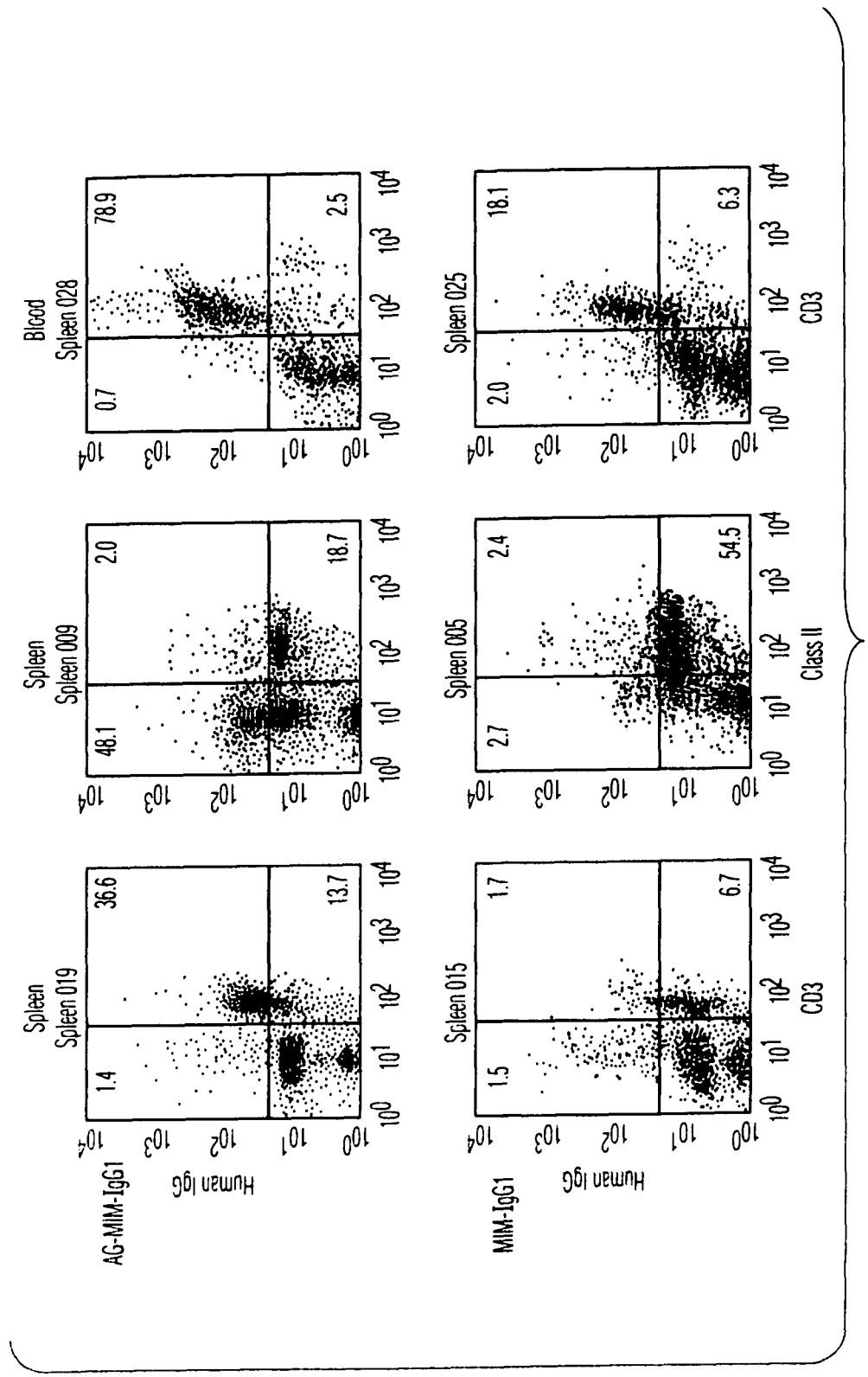

FIG. 3 shows that even though the MIM-IgG1 and AG.MIM-IgG1 antibodies bind poorly to antigen in-vitro, they do bind well to CD52+ cells (in CP-1 transgenic mice) in-vivo. 7 days after the administration of 500 ug of each antibody spleen and blood lymphocytes were analysed by flow cytometry. The figure shows that AG.MIM-IgG1 has bound to the CD3+ cells of the animal. MIM-IgG1 has done the same but clearly some depletion has taken place as the percentage of CD3+ cells in the animals is less (1.7% in spleen vs 36.6% for AG.MIM-IgG1; and 16.1% in blood vs 78.9% for AG.MIM-IgG1).

Figures 4A, 4B:
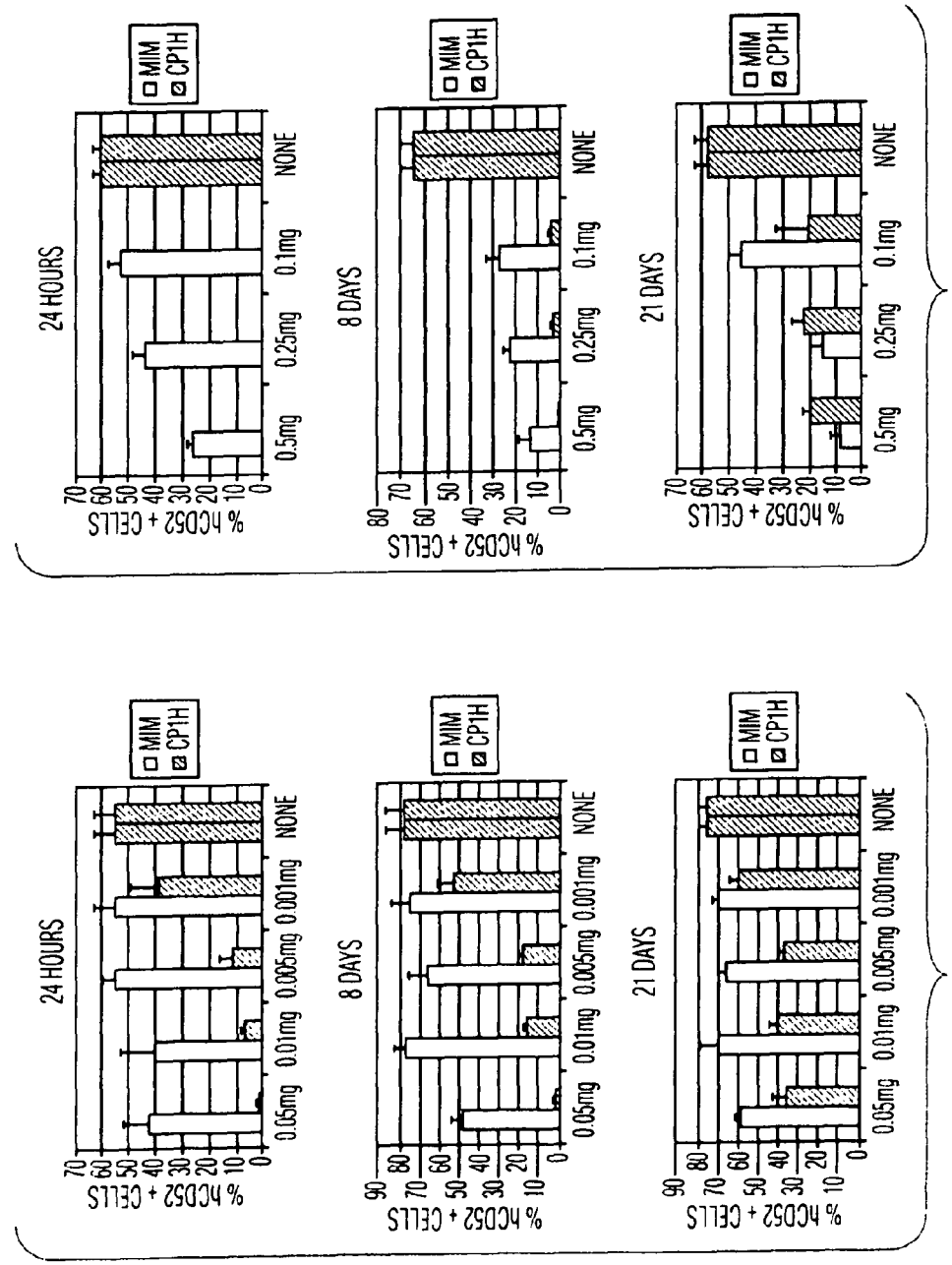

FIG. 4 shows that mimotope-binding form of CAMPATH-1H (MIM-IgG1) is lytic for blood lymphocytes. After the first 24 hrs there is only limited cell-depletion in the blood. However after 7 days it can see that the high doses of MIM-IgG1 antibody do eliminate a significant number of blood lymphocytes. By 1 month the lymphocyte counts in treated hosts are comparable between the two forms of antibody at the high doses (250 μg and 500 μg). The left column (FIG. 4A) shows the level of blood lymphocyte depletion achieved in mice treated with 1 μg to 50 μg of antibody. At these doses, the mimotope-binding form did not deplete while CAMPATH-1H treated animals showed a dose-dependent depletion of T-cells. In the right column (FIG. 4B) CAMPATH-1H shows a fast and efficient depletion of T-cells, whilst the form with bound mimotope achieved a slower depletion that at 7 days was not as complete as with CAMPATH-1H treatment, but was maintained for a longer period. The decrease of hCD52+ cells was not due to coating of the antigen with the injected antibody as the results were confirmed by an equivalent decrease of CD4+ and CD8+ cells.

Figures 5A, 5B:
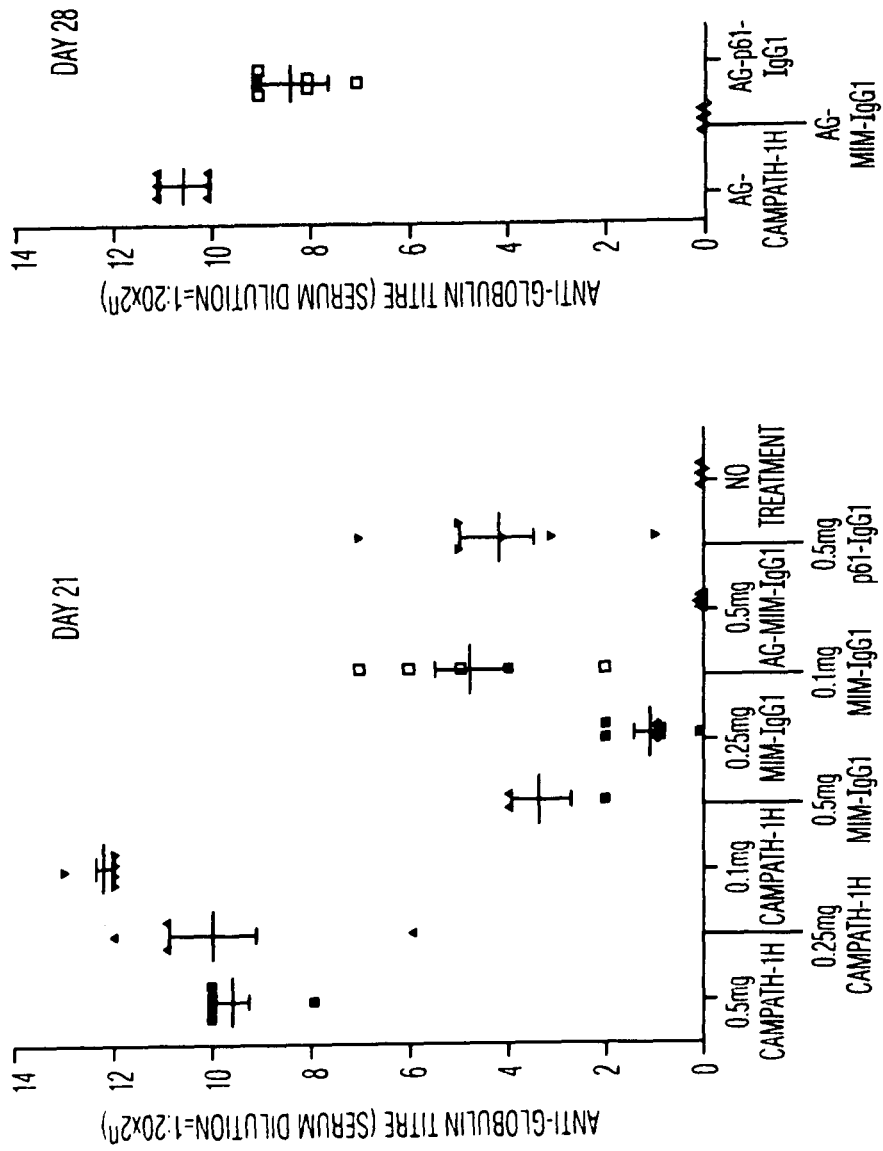

FIG. 5A shows that the mimotope-binding antibody (MIM-IgG1) is poorly immunogenic, and that the aglycosylated form of CAMPATH-1H mimotope is not immunogenic at all. Animals treated with CAMPATH-1H had high titres of anti-CAMPATH-1H Abs, while the titres of mice treated with MIMOTOPE-bound form are far lower. Animals that received the aglycosylated form of the mimotope antibody that is not depleting, had no detectable antiglobulin response. In FIG. 5B it can be seen that the failure of AG.MIM.IgG1 to immunise is not just the result of the mutation to remove the glycosylation of the FC region, as AG-CAMPATH-1H proved very immunogenic. The specificity of the effect for the mimotope was also clearly established as AG-p61-IgG1 was also quite immunogenic.

Figure 6A:
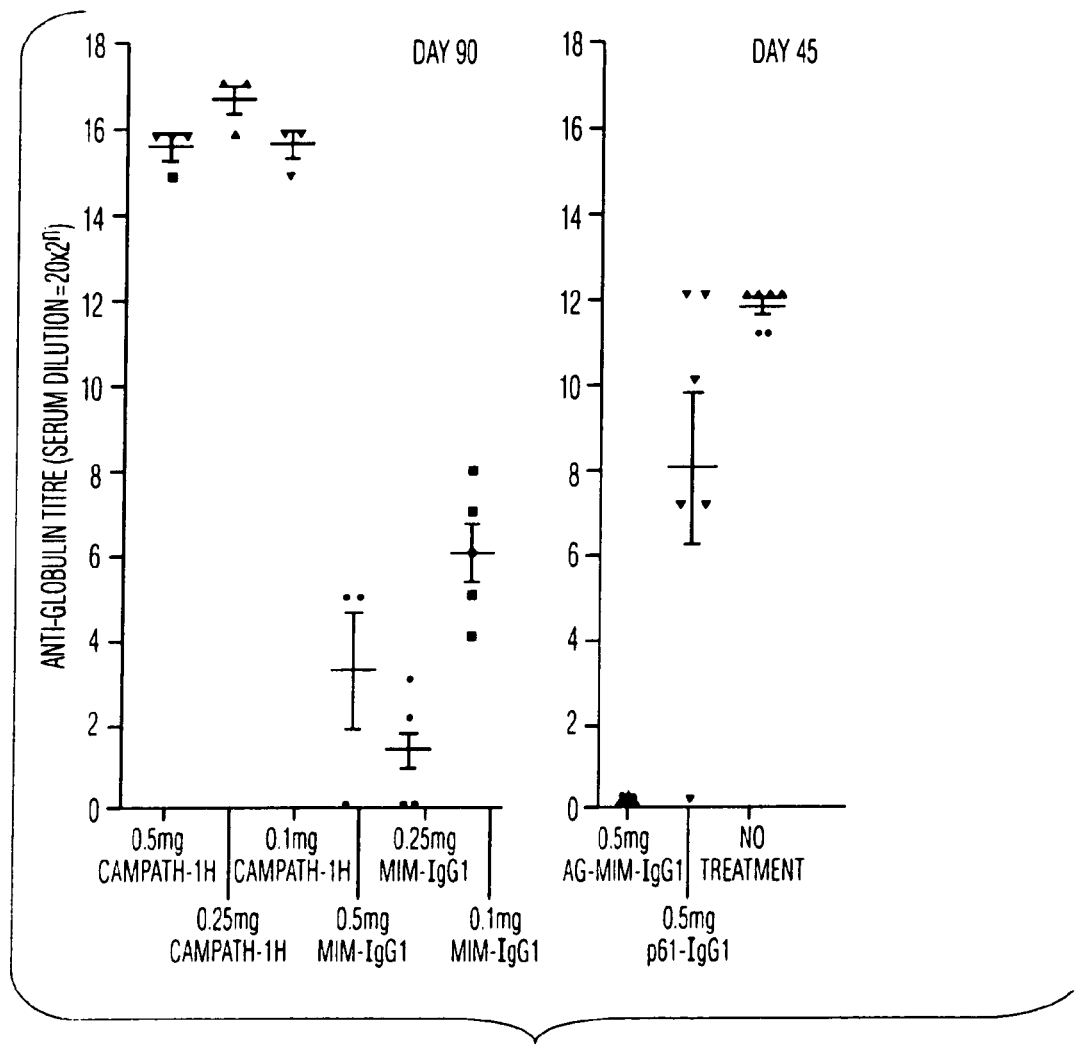

FIG. 6A shows that agylcosylated form of the mimotope-binding CAMPATH-1H antibody (AG.MIM-IgG1) is profoundly tolerogenic. The animals treated at day 0 with CAMPATH-1H linked to the control peptide, or the ones that received no treatment also had high titres of antiglobulin. The mice treated with the mimotope-binding antibody (MIM-IgG1) had much lower titres of antiglobulin, while animals that received the aglycoslylated form of the mimotope-binding antibody (AG.MIM-IgG1) that is not depleting, had no detectable antiglobulin in the sera.

Figure 6B:
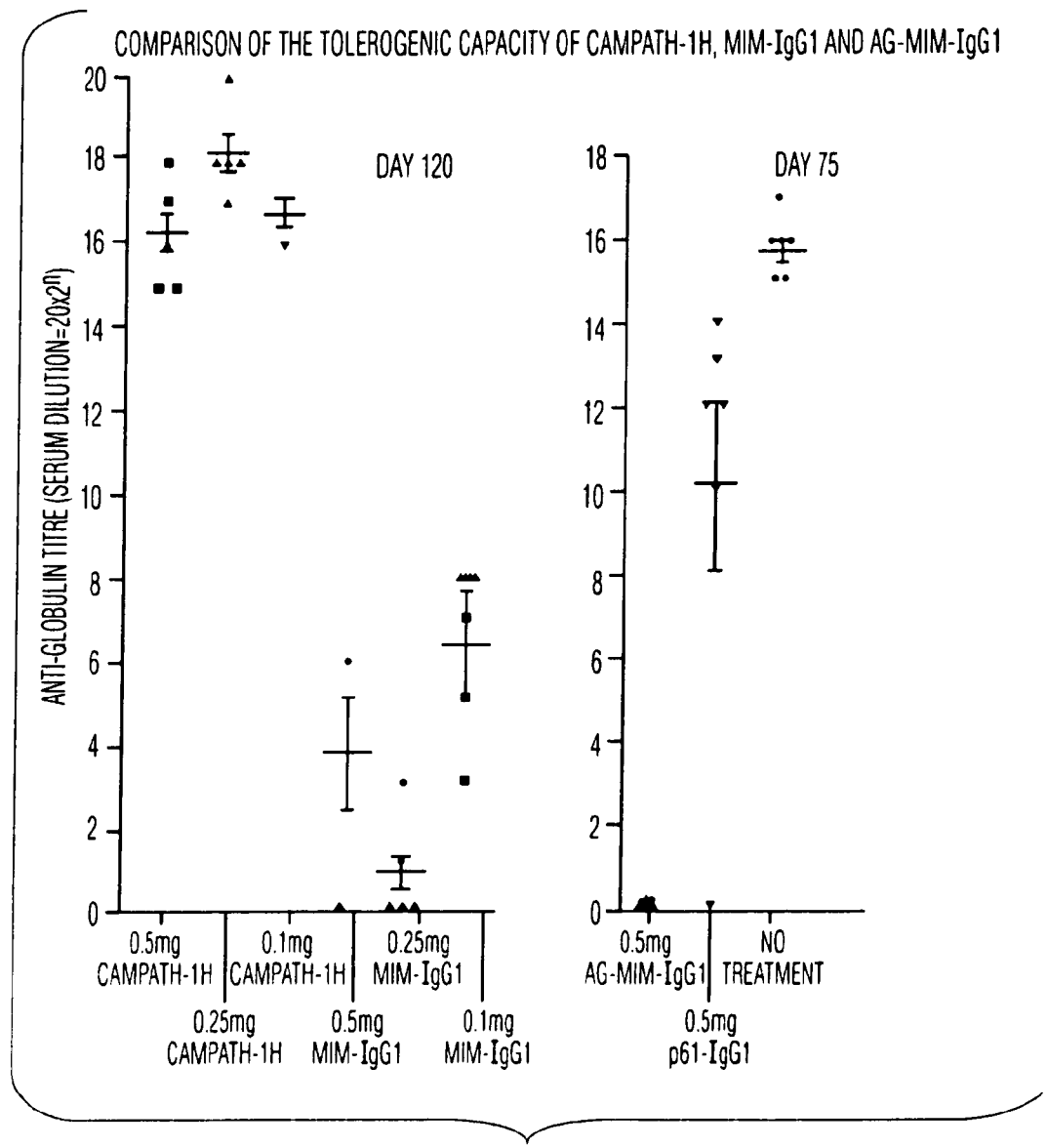

FIG. 6B confirms further that the aglycosylated form of mimotope-binding CAMPATH-1H (AG.MIM-IgG1) is profoundly tolerogenic. The results from FIG. 6B are similar to FIG. 6A with a larger difference in the antiglobulin titres between the groups treated at day 0 with CAMPATH-1H, CAMPATH-1H-p61 or untreated and those groups treated with the mimotope-binding antibodies. Again there were no detectable anti-globulins in mice treated with aglycosyl-form (AG.MIM-IgG1)

Numerous modifications and variations of the embodiments described herein are possible based on the teachings herein; therefore, the scope of the invention is not limited to such embodiments.

The invention claimed is:

1. A process for treating lymphoma or marrow transplant rejection or organ transplant rejection or an autoimmune disease in a mammal, comprising: administering to said mammal a composition comprising (a) an isolated antibody which binds to CD52, said antibody including a light chain, said light chain consisting essentially of amino acid residues 33 through 263 of SEQ ID No: 1; and (b) a pharmaceutically acceptable carrier.

2. The process of claim 1 wherein the antibody is an aglycosylated antibody.

3. The process of claim 2 wherein the Fc portion of the antibody is aglycosylated.

4. The process of claim 1 wherein the antibody does not bind to the Fc receptor.

* * * * *